US010882910B2

(12) United States Patent
Huelsmann et al.

(10) Patent No.: US 10,882,910 B2

(45) Date of Patent: Jan. 5, 2021

(54) EXPRESSION VECTOR ORGANIZATION, NOVEL PRODUCTION CELL GENERATION METHODS AND THEIR USE FOR THE RECOMBINANT PRODUCTION OF POLYPEPTIDES

(71) Applicant: HOFFMANN-LA ROCHE INC., Little Fall, NJ (US)

(72) Inventors: Peter Michael Huelsmann, Habach (DE); Hendrik Knoetgen, Penzberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 208 days.

(21) Appl. No.: 15/948,951

(22) Filed: Apr. 9, 2018

(65) Prior Publication Data

US 2018/0334505 A1 Nov. 22, 2018

Related U.S. Application Data

(62) Division of application No. 14/367,043, filed as application No. PCT/EP2012/076167 on Dec. 19, 2012, now Pat. No. 9,963,511.

(30) Foreign Application Priority Data

Dec. 22, 2011 (EP) .................................... 11195363

(51) Int. Cl.

*C07K 16/28* (2006.01)

*C07K 16/00* (2006.01)

(52) U.S. Cl.

CPC .......... *C07K 16/2854* (2013.01); *C07K 16/00* (2013.01)

(58) Field of Classification Search

None

See application file for complete search history.

(56) References Cited

U.S. PATENT DOCUMENTS

| | | | | |
|---|---|---|---|---|
| 5,731,168 | A | 3/1998 | Carter et al. | |
| 9,102,971 | B2 | 8/2015 | Kurokawa et al. | |
| 2004/0033561 | A1 | 2/2004 | O'Keefe et al. | |
| 2008/0241883 | A1 | 10/2008 | Gion et al. | |
| 2014/0370547 | A1 | 12/2014 | Huelsmann et al. | |
| 2018/0334505 | A1 * | 11/2018 | Huelsmann ............ | C07K 16/00 |

FOREIGN PATENT DOCUMENTS

| | | | |
|---|---|---|---|
| CN | 100999732 | A | 7/2007 |
| CN | 101550425 | A | 10/2009 |
| CN | 101596316 | A | 12/2009 |
| EA | 7905 | B1 | 2/2007 |
| EP | 1331266 | A1 | 7/2003 |
| EP | 1392835 | B1 | 10/2009 |
| EP | 2439269 | A1 | 4/2012 |
| JP | H04504365 | A | 8/1992 |
| JP | H09507753 | A | 8/1997 |
| JP | 2000500334 | A | 1/2000 |
| JP | 2002525047 | A | 8/2002 |
| JP | 2005522225 | A | 7/2005 |
| JP | 2006271394 | A | 10/2006 |
| JP | 2010529833 | A | 9/2010 |
| JP | 2011109509 | A | 6/2011 |
| JP | 2011525808 | A | 9/2011 |
| WO | WO 1991010741 | A1 | 7/1991 |
| WO | 9308829 | A1 | 5/1993 |
| WO | WO 1995017911 | A1 | 7/1995 |
| WO | WO 1997017446 | A2 | 5/1997 |
| WO | WO 1997017446 | A3 | 5/1997 |
| WO | WO 2000015772 | A2 | 3/2000 |
| WO | WO 2000015772 | A3 | 3/2000 |
| WO | WO 2000015772 | A3 | 7/2000 |
| WO | WO 2000040737 | A1 | 7/2000 |
| WO | 0162801 | A2 | 8/2001 |
| WO | 0188159 | A2 | 11/2001 |
| WO | WO 2002060955 | A2 | 8/2002 |
| WO | WO 2002060955 | A3 | 8/2002 |
| WO | 02070648 | A1 | 9/2002 |
| WO | 2002101006 | A2 | 12/2002 |
| WO | WO 2000040737 | A1 | 6/2003 |
| WO | WO 2003087828 | A1 | 10/2003 |
| WO | 2004061104 | A2 | 7/2004 |
| WO | 2004092219 | A2 | 10/2004 |
| WO | 2005089285 | A2 | 9/2005 |
| WO | 2006009746 | A2 | 1/2006 |

(Continued)

OTHER PUBLICATIONS

The English translation of the Brazilian Office Action, dated Jul. 30, 2019, in the related Brazilian Appl. No. 112014012667-4.

The English translation of the Korean Office Action, dated Feb. 18, 2019, in the related Korean Appl. No. 10-2014-7016980.

Milstein et al., "Hybrid hybridomas and their use in immunohistochemistry," Nature vol. 305, pp. 537-540, (1983).

Traunecker et al., "Bispecific single chain molecules (Janusins) target cytotoxic lymphocytes on HIV infected cells," The EMBO Journal vol. 10, pp. 3655-3659, (1991).

Buchman et al., "Comparison of intron-dependent and intron-independent gene expression", Mol Cell Biol, 8(10):4395-4405 (1988).

Cacciatore et al., "Gene amplification and vector engineering to achieve rapid and high-level therapeutic protein production using the Dhfr-based CHO cell selection system", Biotechnol Adv., 28(6):673-681 (2010).

(Continued)

*Primary Examiner* — Michael D Burkhart

(57) ABSTRACT

Herein is reported an expression vector comprising —an antibody light chain expression cassette, —an antibody heavy chain expression cassette, and —a selection marker expression cassette, wherein the expression cassettes are arranged unidirectional, and wherein the expression cassettes are arranged in the 5' to 3' sequence of antibody heavy chain expression cassette, antibody light chain expression cassette and selection marker expression cassette. Further are reported herein methods for the generation of antibody producing cells and the use of these cells for the recombinant production of antibodies.

17 Claims, 12 Drawing Sheets

Figure 1:
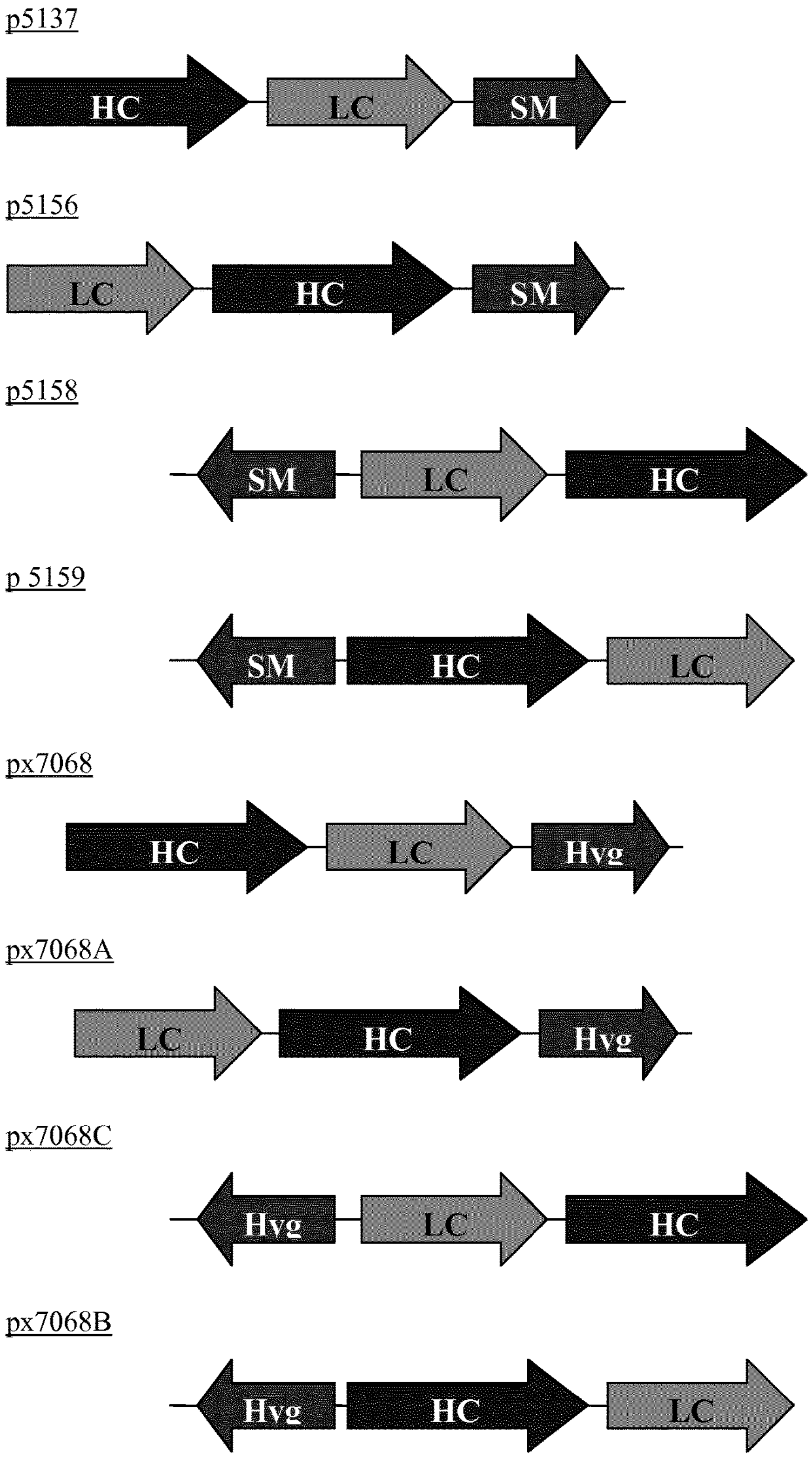

Specification includes a Sequence Listing.

(56) References Cited

FOREIGN PATENT DOCUMENTS

| | | | |
|---|---|---|---|
| WO | 2006125126 | A2 | 11/2006 |
| WO | 2007045465 | A1 | 4/2007 |
| WO | 2008077545 | A1 | 7/2008 |
| WO | WO 2008142124 | A1 | 11/2008 |
| WO | 2009003622 | A1 | 1/2009 |
| WO | WO 2009046978 | A1 | 4/2009 |
| WO | WO 2009157771 | A2 | 12/2009 |
| WO | WO 2009157771 | A3 | 12/2009 |
| WO | 2010/022961 | A1 | 3/2010 |
| WO | 2010022961 | A1 | 3/2010 |
| WO | WO 2010053716 | A1 | 5/2010 |
| WO | WO 2010097437 | A1 | 9/2010 |
| WO | WO 2011033375 | A2 | 3/2011 |
| WO | WO 2011033375 | A3 | 3/2011 |
| WO | 2012017003 | A1 | 2/2012 |
| WO | 2015092735 | A1 | 6/2015 |

OTHER PUBLICATIONS

Costa et al., "Guidelines to cell engineering for monoclonal antibody production", Eur J Pharm Biopharm, 74(2):127-138 (2010).

Fu et al., "Linear transgene constructs lacking vector backbone sequences generate low-copy-number transgenic plants with simple integration patterns", Transgenic Res., 9(1):11-19 (2000).

Higuchi et al., "Cell display library for gene cloning of variable regions of human antibodies to hepatitis B surface antigen", J Immunol Methods, 202(2):193-204 (1997).

Ho et al., "IRES-mediated Tricistronic vectors for enhancing generation of high monoclonal antibody expressing CHO cell lines", J Biotechnol., 157(1):130-139 (2012).

Hotta et al., "Production of anti-CD2 chimeric antibody by recombinant animal cells", J Biosci Bioeng., 98(4):298-303 (2004).

Kennard et al., "The Generation of Stable, High MAb Expressing CHO Cell Lines Based on the Artificial Chromosome Expression (ACE) Technology", Biotechnol Bioeng., 104(3):540-553 (2009).

Kim et al., "Improved mammalian expression systems by manipulating transcriptional termination regions", Biotechnol Prog., 19(5):1620-1622 (2003).

Kim et al., "Use of the human elongation factor 1 alpha promoter as a versatile and efficient expression system", Gene., 91(2):217-223 (1990).

Lee et al., "High-efficiency protein expression mediated by enterovirus 71 internal ribosome entry site", Biotechnol Bioeng., 90(5):656-662 (2005).

Li et al., "A comparative study of different vector designs for the mammalian expression of recombinant IgG antibodies", J Immunol Methods, 318(1-2):113-124 (2007).

McLean et al., "Human and murine immunoglobulin expression vector cassettes", Mol Immunol., 37(14):837-845 (2000).

Palmitter et al., "Germ-line transformation of mice", Annu Rev Genet, 20:465-499 (1986).

Sanna, "Expression of antibody Fab fragments and whole immunoglobulin in mammalian cells", Methods Mol Biol., 178:389-395 (2002).

Schlatter et al., "On the optimal ratio of heavy to light chain genes for efficient recombinant antibody production by CHO cells", Biotechnology Prgress, 21(1):122-133 (2005).

Townes et al., "Erythroid-specific expression of human beta-globin genes in transgenic mice", EMBO J., 4(7):1715-1723 (1985).

Wang et al., "Chapter 25 Antibody expression in mammalian cells" In: "Therapeutic monoclonal antibodies—From bench to clinic", pp. 557-572 (2009).

Winnard et al., "Robust expression of transgenes in MCF-7 breast cancer cells is expression vector-dependent", Biotechniques., 37(3):370, 372, 374 (2004).

Yew et al., "Optimization of plasmid vectors for high-level expression in lung epithelial cells", Hum Gene Ther., 8(5):575-584 (1997).

The English translation of the Korean OA, mailed on Feb. 11, 2019, in the related Korean Appl. No. 10-2014-7016825.

The International Search Report & Written Opinion, dated Aug. 13, 2013, in the related PCT Appl. No. PCT/EP2012/076203.

The International Search Report & Written Opinion, dated Jun. 13, 2013, in the related PCT Appl. No. PCT/EP2012/076167.

The Office Actions, dated Jun. 6 & Aug. 30, 2016, Mar. 15, 2017 and Aug. 16, 2019 , in the related U.S. Appl. No. 14/367,680.

The English translation of the Japanese Office Action, dated Feb. 5, 2020, in the related Japanese Appl. No. 2019-012157.

Gillies et al., "Expression of Human Anti-Tetanus Toxoid Antibody in Transfected Murine Myeloma Cells," Bio/Technology vol. 7, pp. 799-804(1989). Abstract.

U.S. Office Actions, dated Mar. 2 and May 14, 2020, in the related U.S. Appl. No. 14/367,680.

The Chinese Office Action, dated Apr. 10, 2020, in the related Chinese Patent Appl. No. 201710324350.7.

D4: Gong, Y., et al., "Effect of Chimeric Intron on the Expression of Anti-bFGF Antibody Genes in 293T Cells," China Biotechnol, vol. 30 Issue 3, pp. 9-14. (English Abstract).

The Chinese Office Action, dated Jul. 31, 2020, in the related Chinese Patent Appl. No. 201711133954.X.

Wu et al., "Construction and identification of eukaryotic expression vectors bearing the gene of human antibody against HFRS virus," Journal of Cellular and Molecular Immunology, vol. 16, No. 1, pp. 20-22. Dec. 31, 2000. (English abstract included.).

The English translation of the Korean Office Action, dated Aug. 18, 2020, in the related Korean Patent Appl. No. 10-2020-7007391.

Sibler et al., "Extended half-life upon binding of destabilized intrabodies allows specific detection of antigen in mammalian cells," FEBS Journal, 272: 2878-2891, May 20, 2005.

* cited by examiner (A)

(B)

(C)

(D)

(E)

SEQUENCE LISTING

```
<160> NUMBER OF SEQ ID NOS: 17

<210> SEQ ID NO 1
<211> LENGTH: 608
<212> TYPE: DNA
<213> ORGANISM: Human cytomegalovirus

<400> SEQUENCE: 1

gttgacattg attattgact agttattaat agtaatcaat tacggggtca ttagttcata     60

gcccatatat ggagttccgc gttacataac ttacggtaaa tggcccgcct ggctgaccgc    120

ccaacgaccc ccgcccattg acgtcaataa tgacgtatgt tcccatagta acgccaatag    180

ggactttcca ttgacgtcaa tgggtggagt atttacggta aactgcccac ttggcagtac    240

atcaagtgta tcatatgcca agtacgcccc ctattgacgt caatgacggt aaatggcccg    300

cctggcatta tgcccagtac atgaccttat gggactttcc tacttggcag tacatctacg    360

tattagtcat cgctattagc atggtgatgc ggttttggca gtacatcaat gggcgtggat    420

agcggtttga ctcacgggga tttccaagtc tccaccccat tgacgtcaat gggagtttgt    480

tttggcacca aaatcaacgg gactttccaa aatgtcgtaa caactccgcc ccattgacgc    540

aaatgggcgg taggcgtgta cggtgggagg tctatataag cagagctccg tttagtgaac    600

gtcagatc                                                              608


<210> SEQ ID NO 2
<211> LENGTH: 696
<212> TYPE: DNA
<213> ORGANISM: Human cytomegalovirus

<400> SEQUENCE: 2

gttgacattg attattgact agttattaat agtaatcaat tacggggtca ttagttcata     60

gcccatatat ggagttccgc gttacataac ttacggtaaa tggcccgcct ggctgaccgc    120

ccaacgaccc ccgcccattg acgtcaataa tgacgtatgt tcccatagta acgccaatag    180

ggactttcca ttgacgtcaa tgggtggagt atttacggta aactgcccac ttggcagtac    240

atcaagtgta tcatatgcca agtacgcccc ctattgacgt caatgacggt aaatggcccg    300

cctggcatta tgcccagtac atgaccttat gggactttcc tacttggcag tacatctacg    360

tattagtcat cgctattagc atggtgatgc ggttttggca gtacatcaat gggcgtggat    420
```

agcggtttga ctcacgggga tttccaagtc tccaccccat tgacgtcaat gggagtttgt 480
tttggcacca aaatcaacgg gactttccaa aatgtcgtaa caactccgcc ccattgacgc 540
aaatgggcgg taggcgtgta cggtgggagg tctatataag cagagctccg tttagtgaac 600
gtcagatcta gctctgggag aggagcccag cactagaagt cggcggtgtt tccattcggt 660
gatcagcact gaacacagag gaagcttgcc gccacc 696

<210> SEQ ID NO 3
<211> LENGTH: 2125
<212> TYPE: DNA
<213> ORGANISM: Human cytomegalovirus

<400> SEQUENCE: 3
ctgcagtgaa taataaaatg tgtgtttgtc cgaaatacgc gttttgagat ttctgtcgcc 60
gactaaattc atgtcgcgcg atagtggtgt ttatcgccga tagagatggc gatattggaa 120
aaatcgatat ttgaaaatat ggcatattga aaatgtcgcc gatgtgagtt tctgtgtaac 180
tgatatcgcc atttttccaa aagtgatttt tgggcatacg cgatatctgg cgatagcgct 240
tatatcgttt acgggggatg gcgatagacg actttggtga cttgggcgat tctgtgtgtc 300
gcaaatatcg cagtttcgat ataggtgaca gacgatatga ggctatatcg ccgatagagg 360
cgacatcaag ctggcacatg gccaatgcat atcgatctat acattgaatc aatattggcc 420
attagccata ttattcattg gttatatagc ataaatcaat attggctatt ggccattgca 480
tacgttgtat ccatatcata atatgtacat ttatattggc tcatgtccaa cattaccgcc 540
atgttgacat tgattattga ctagttatta atagtaatca attacggggt cattagttca 600
tagcccatat atggagttcc gcgttacata acttacggta aatggcccgc ctggctgacc 660
gcccaacgac ccccgcccat tgacgtcaat aatgacgtat gttcccatag taacgccaat 720
agggactttc cattgacgtc aatgggtgga gtatttacgg taaactgccc acttggcagt 780
acatcaagtg tatcatatgc caagtacgcc ccctattgac gtcaatgacg gtaaatggcc 840
cgcctggcat tatgcccagt acatgacctt atgggacttt cctacttggc agtacatcta 900
cgtattagtc atcgctatta ccatggtgat gcggttttgg cagtacatca atgggcgtgg 960
atagcggttt gactcacggg gatttccaag tctccacccc attgacgtca atgggagttt 1020
gttttggcac caaaatcaac gggactttcc aaaatgtcgt aacaactccg ccccattgac 1080
gcaaatgggc ggtaggcgtg tacggtggga ggtctatata agcagagctc gtttagtgaa 1140
ccgtcagatc gcctggagac gccatccacg ctgttttgac ctccatagaa gacaccggga 1200
ccgatccagc ctccgcggcc gggaacggtg cattggaacg cggattcccc gtgccaagag 1260
tgacgtaagt accgcctata gagtctatag gcccaccccc ttggcttctt atgcatgcta 1320
tactgttttt ggcttggggt ctatacaccc ccgcttcctc atgttatagg tgatggtata 1380
gcttagccta taggtgtggg ttattgacca ttattgacca ctcccctatt ggtgacgata 1440
ctttccatta ctaatccata acatggctct ttgccacaac tctctttatt ggctatatgc 1500
caatacactg tccttcagag actgacacgg actctgtatt tttacaggat ggggtctcat 1560
ttattattta caaattcaca tatacaacac caccgtcccc agtgcccgca gtttttatta 1620
aacataacgt gggatctcca cgcgaatctc gggtacgtgt tccggacatg ggctcttctc 1680
cggtagcggc ggagcttcta catccgagcc ctgctcccat gcctccagcg actcatggtc 1740
gctcggcagc tccttgctcc taacagtgga ggccagactt aggcacagca cgatgcccac 1800

-continued caccaccagt gtgccgcaca aggccgtggc ggtagggtat gtgtctgaaa atgagctcgg 1860
ggagcgggct tgcaccgctg acgcatttgg aagacttaag gcagcggcag aagaagatgc 1920
aggcagctga gttgttgtgt tctgataaga gtcagaggta actcccgttg cggtgctgtt 1980
aacggtggag ggcagtgtag tctgagcagt actcgttgct gccgcgcgcg ccaccagaca 2040
taatagctga cagactaaca gactgttcct ttccatgggt cttttctgca gtcaccgtcc 2100
ttgacacggt ttaaacgccg ccacc 2125

<210> SEQ ID NO 4
<211> LENGTH: 575
<212> TYPE: DNA
<213> ORGANISM: Homo sapiens

<400> SEQUENCE: 4
cccgggctgg gctgagaccc gcagaggaag acgctctagg gatttgtccc ggactagcga 60
gatggcaagg ctgaggacgg gaggctgatt gagaggcgaa ggtacaccct aatctcaata 120
caacctttgg agctaagcca gcaatggtag agggaagatt ctgcacgtcc cttccaggcg 180
gcctccccgt caccaccccc cccaacccgc cccgaccgga gctgagagta attcatacaa 240
aaggactcgc ccctgccttg gggaatccca gggaccgtcg ttaaactccc actaacgtag 300
aacccagaga tcgctgcgtt cccgccccct cacccgcccg ctctcgtcat cactgaggtg 360
gagaagagca tgcgtgaggc tccggtgccc gtcagtgggc agagcgcaca tcgcccacag 420
tccccgagaa gttgggggga ggggtcggca attgaaccgg tgcctagaga aggtggcgcg 480
gggtaaactg ggaaagtgat gtcgtgtact ggctccgcct ttttcccgag ggtgggggag 540
aaccgtatat aagtgcagta gtcgccgtga acgtt 575

<210> SEQ ID NO 5
<211> LENGTH: 1571
<212> TYPE: DNA
<213> ORGANISM: Homo sapiens

<400> SEQUENCE: 5
cccgggctgg gctgagaccc gcagaggaag acgctctagg gatttgtccc ggactagcga 60
gatggcaagg ctgaggacgg gaggctgatt gagaggcgaa ggtacaccct aatctcaata 120
caacctttgg agctaagcca gcaatggtag agggaagatt ctgcacgtcc cttccaggcg 180
gcctccccgt caccaccccc cccaacccgc cccgaccgga gctgagagta attcatacaa 240
aaggactcgc ccctgccttg gggaatccca gggaccgtcg ttaaactccc actaacgtag 300
aacccagaga tcgctgcgtt cccgccccct cacccgcccg ctctcgtcat cactgaggtg 360
gagaagagca tgcgtgaggc tccggtgccc gtcagtgggc agagcgcaca tcgcccacag 420
tccccgagaa gttgggggga ggggtcggca attgaaccgg tgcctagaga aggtggcgcg 480
gggtaaactg ggaaagtgat gtcgtgtact ggctccgcct ttttcccgag ggtgggggag 540
aaccgtatat aagtgcagta gtcgccgtga acgttctttt tcgcaacggg tttgccgcca 600
gaacacaggt aagtgccgtg tgtggttccc gcgggcctgg cctctttacg ggttatggcc 660
cttgcgtgcc ttgaattact tccacgcccc tggctgcagt acgtgattct tgatcccgag 720
cttcgggttg gaagtgggtg ggagagttcg aggccttgcg cttaaggagc cccttcgcct 780
cgtgcttgag ttgaggcctg gcctgggcgc tggggccgcc gcgtgcgaat ctggtggcac 840
cttcgcgcct gtctcgctgc tttcgataag tctctagcca tttaaaattt ttgatgacct 900
gctgcgacgc tttttttctg gcaagatagt cttgtaaatg cgggccaaga tctgcacact 960

```
ggtatttcgg tttttggggc cgcgggcggc gacggggccc gtgcgtccca gcgcacatgt   1020

tcggcgaggc ggggcctgcg agcgcggcca ccgagaatcg gacgggggta gtctcaagct   1080

ggccggcctg ctctggtgcc tggcctcgcg ccgccgtgta tcgccccgcc ctgggcggca   1140

aggctggccc ggtcggcacc agttgcgtga gcggaaagat ggccgcttcc cggccctgct   1200

gcagggagct caaaatggag gacgcggcgc tcgggagagc gggcgggtga gtcacccaca   1260

caaaggaaaa gggcctttcc gtcctcagcc gtcgcttcat gtgactccac ggagtaccgg   1320

gcgccgtcca ggcacctcga ttagttctcg atcttttgga gtacgtcgtc tttaggttgg   1380

ggggaggggt tttatgcgat ggagtttccc cacactgagt gggtggagac tgaagttagg   1440

ccagcttggc acttgatgta attctccttg gaatttgccc tttttgagtt tggatcttgg   1500

ttcattctca agcctcagac agtggttcaa agtttttttc ttccatttca ggtggtttaa   1560

acgccgccac c                                                        1571
```

<210> SEQ ID NO 6
<211> LENGTH: 1653
<212> TYPE: DNA
<213> ORGANISM: Artificial Sequence
<220> FEATURE:
<223> OTHER INFORMATION: human elongation factor 1 alpha promoter with Intron A and with optimized 5'UTR

<400> SEQUENCE: 6

```
cccgggctgg gctgagaccc gcagaggaag acgctctagg gatttgtccc ggactagcga     60

gatggcaagg ctgaggacgg gaggctgatt gagaggcgaa ggtacaccct aatctcaata    120

caacctttgg agctaagcca gcaatggtag agggaagatt ctgcacgtcc cttccaggcg    180

gcctccccgt caccaccccc cccaacccgc cccgaccgga gctgagagta attcatacaa    240

aaggactcgc ccctgccttg gggaatccca gggaccgtcg ttaaactccc actaacgtag    300

aacccagaga tcgctgcgtt cccgccccct cacccgcccg ctctcgtcat cactgaggtg    360

gagaagagca tgcgtgaggc tccggtgccc gtcagtgggc agagcgcaca tcgcccacag    420

tccccgagaa gttgggggga ggggtcggca attgaaccgg tgcctagaga aggtggcgcg    480

gggtaaactg ggaaagtgat gtcgtgtact ggctccgcct ttttcccgag ggtgggggag    540

aaccgtatat aagtgcagta gtcgccgtga acgttctttt tcgcaacggg tttgccgcca    600

gaacacaggt aagtgccgtg tgtggttccc gcgggcctgg cctctttacg ggttatggcc    660

cttgcgtgcc ttgaattact tccacgcccc tggctgcagt acgtgattct tgatcccgag    720

cttcgggttg gaagtgggtg ggagagttcg aggccttgcg cttaaggagc cccttcgcct    780

cgtgcttgag ttgaggcctg gcctgggcgc tggggccgcc gcgtgcgaat ctggtggcac    840

cttcgcgcct gtctcgctgc tttcgataag tctctagcca tttaaaattt ttgatgacct    900

gctgcgacgc tttttttctg gcaagatagt cttgtaaatg cgggccaaga tctgcacact    960

ggtatttcgg tttttggggc cgcgggcggc gacggggccc gtgcgtccca gcgcacatgt   1020

tcggcgaggc ggggcctgcg agcgcggcca ccgagaatcg gacgggggta gtctcaagct   1080

ggccggcctg ctctggtgcc tggcctcgcg ccgccgtgta tcgccccgcc ctgggcggca   1140

aggctggccc ggtcggcacc agttgcgtga gcggaaagat ggccgcttcc cggccctgct   1200

gcagggagct caaaatggag gacgcggcgc tcgggagagc gggcgggtga gtcacccaca   1260

caaaggaaaa gggcctttcc gtcctcagcc gtcgcttcat gtgactccac ggagtaccgg   1320

gcgccgtcca ggcacctcga ttagttctcg atcttttgga gtacgtcgtc tttaggttgg   1380
```

```
ggggaggggt tttatgcgat ggagtttccc cacactgagt gggtggagac tgaagttagg   1440
ccagcttggc acttgatgta attctccttg gaatttgccc tttttgagtt tggatcttgg   1500
ttcattctca agcctcagac agtggttcaa agtttttttc ttccatttca ggtgtcgtga   1560
ggaattagct ctgggagagg agcccagcac tagaagtcgg cggtgtttcc attcggtgat   1620
cagcactgaa cacagaggaa gcttgccgcc acc                                1653
```

<210> SEQ ID NO 7
<211> LENGTH: 2473
<212> TYPE: DNA
<213> ORGANISM: Rattus norvegicus

<400> SEQUENCE: 7

```
gatattttta tggaaatttt aaaaaattct ggtaagctat ttaaaaaaat gaactttatt     60
atgaaactat tgccctttc tctaaaaaac aacacaattt cacggaatat cctatgatta    120
attatgacct tttagccagt tcccatatta agaatgagtt atagatgact ctctttaaaa    180
aattattcga tttaaaccat ctgttttaaa gcacagcatt tgtgaataat gtgaagaact    240
tagaagtata atctactcca aggtctgatg tatttttcaa ggccacgtta aagtgtatgc    300
ttgtaacaga gtgcttacat tcaagccaaa tgttaatata acaatcctga attcgtacat    360
aatgtgaata agacactcaa ctctatttaa atccagatct aaatagttac ttttatctaa    420
atgtcaccat ctgtttctac ttagaataat aaacttctta aaggtcacgt atcgggctga    480
ttataaatca ttataattat aacaaaacag atgatttgtt taaaggtcac atcccgttcc    540
gtggtctttt tagtcgaaat aactattaat cttcattatg tttctgagaa agtttaaata    600
tcacgatttc cacccataac agtcattatg agtcagtggg agtcatactg aatcagggta    660
ttttaactgg aaatttttttg aaaaacatga gtttttctta aggtcaacat ctggtcttat    720
aaacagaact gagatttatg gccggtaatt accactggac gatttcccgg gaaatcgcta    780
tgggaacggc ccgttttgca acttctttga ccaaaatata tcgagttaag caacttttaa    840
ggccaagtca ctatgactat gccaaataaa gcaactatta aggtcatttc actatggaaa    900
cacccaattc agcaacattg taagccaaat ctccatagaa acctcataag tcagccaaaa    960
gtcaacgacc taccatctgt ttctgcttat ttctctaatt ttaattgcag actttgtcat   1020
tttatgttcc tcttattctg agaatacgtg acgcccgctc gttaaggaca ccgaaactgc   1080
ataagagtca cgttgactca gatgacctcg acatctggtc tggtttttct gccaattttt   1140
cgtctaaact gtggaaaatc cccacagatg acctacaaaa ctccgatttc tattggacga   1200
tgaccgtcag acgtaggtat aaatctccta acgccgttcg ggcagtcaca gtcttcggat   1260
cggacgccgt ggaacgcagt tctcagcgaa gaaggacacc gcccgactcc agaagacacc   1320
gctgcccgaa gaagagaaga cttcatcggt aagagaccca gcttctcctc cccggagctt   1380
cggccacgcc gctccacacc cgggaaccga ggcttcggag cccgataccc ggacagaagc   1440
ttctccccgg ccgctccaca tcagggagcc ttgaccggcg agcctgctat ccgggtagag   1500
actgtcctgc ggccgcttca gcagctccac gatcgacgac tgtgaccgtt gagcccgccg   1560
tttaggcaga ggctccgctt caactaccct accgacacat tcgcggttct tcctccagaa   1620
catcttaccc tctactcggc cactctacaa ggaccggtaa gcaattttta tatactagac   1680
ttaaatgttt ctatgatcat tatgtggtga tggttctgtg tatgaagaga gctaggtgga   1740
ggctatcttt cgcttcggtg atggaacact actcttacaa tggcggctct aatgacggtt   1800
```

ttctcaacat cggtggcggc tctaattacg gttctctcaa catcggtggt ggtcttcgca 1860
tgcgagctct agattttttt tatctgtaaa ataagattga agatggttga ctgtgtatca 1920
attctttttc ataggcatca gatcttgtca accgttatta atctttagga tcagatgaac 1980
ttgcgagctc gatatctaga atagaatccc cgtgactgct aagatcatct ccgttcatac 2040
accagatgtt acaggccacg gctaccatta tgaatccaaa catgaacaga attgccagaa 2100
tggtgctcaa tggttgtatc catctcgctg gtctattttc tctcaccgac gagaccccaa 2160
catcgagagt tccgtttatt tcatgagtcg accttttagt tcgtgattta ttttctgtgt 2220
taagaaaatc agtgagatca attattgtca gtctatacga ttacaataat gtctgaatta 2280
tcgacgtgca taagatcgtc tcacccggcg cagattccaa cagatctttg tcgccatgcc 2340
ttccgttaga aaggtagtat agtaatatga taccagcaat gcacagaatc gaacatttga 2400
taacaatttt gttgatgtcg tatatctgtt aaaaattaat aaatatatta cagtcagttt 2460
aaacgccgcc acc 2473

<210> SEQ ID NO 8
<211> LENGTH: 129
<212> TYPE: DNA
<213> ORGANISM: Simian virus 40

<400> SEQUENCE: 8
aacttgttta ttgcagctta taatggttac aaataaagca atagcatcac aaatttcaca 60
aataaagcat ttttttcacc attctagttg tggtttgtcc aaactcatca atgtatctta 120
tcatgtctg 129

<210> SEQ ID NO 9
<211> LENGTH: 225
<212> TYPE: DNA
<213> ORGANISM: Bos taurus

<400> SEQUENCE: 9
ctgtgccttc tagttgccag ccatctgttg tttgcccctc ccccgtgcct tccttgaccc 60
tggaaggtgc cactcccact gtcctttcct aataaaatga ggaaattgca tcgcattgtc 120
tgagtaggtg tcattctatt ctggggggtg gggtggggca ggacagcaag ggggaggatt 180
gggaagacaa tagcaggcat gctggggatg cggtgggctc tatgg 225

<210> SEQ ID NO 10
<211> LENGTH: 73
<212> TYPE: DNA
<213> ORGANISM: Homo sapiens

<400> SEQUENCE: 10
caggataata tatggtaggg ttcatagcca gagtaacctt tttttttaat ttttatttta 60
ttttattttt gag 73

<210> SEQ ID NO 11
<211> LENGTH: 288
<212> TYPE: DNA
<213> ORGANISM: Simian virus 40

<400> SEQUENCE: 11
agtcagcaac caggtgtgga aagtccccag gctccccagc aggcagaagt atgcaaagca 60
tgcatctcaa ttagtcagca accatagtcc cgcccctaac tccgcccatc ccgcccctaa 120
ctccgcccag ttccgcccat tctccgcccc atggctgact aatttttttt atttatgcag 180
aggccgaggc cgcctctgcc tctgagctat tccagaagta gtgaggaggc ttttttggag 240
gcctaggctt ttgcaaaaag ctcccgggag cttgtatatc cattttcg 288

<210> SEQ ID NO 12
<211> LENGTH: 81
<212> TYPE: DNA
<213> ORGANISM: Homo sapiens

<400> SEQUENCE: 12
catggcttcc cgccggaggt ggaggagcag gatgatggca cgctgcccat gtcttgtgcc 60
caggagagcg ggatggaccg t 81

<210> SEQ ID NO 13
<211> LENGTH: 798
<212> TYPE: DNA
<213> ORGANISM: Artificial Sequence
<220> FEATURE:
<223> OTHER INFORMATION: green fluorescent protein encoding nucleic acid

<400> SEQUENCE: 13
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtcc 720
ggactcagat ctcgagctca agcttcgaat tctgcagtcg acggtaccgc gggcccggga 780
tccaccggat ctagatga 798

<210> SEQ ID NO 14
<211> LENGTH: 795
<212> TYPE: DNA
<213> ORGANISM: Artificial Sequence
<220> FEATURE:
<223> OTHER INFORMATION: neomycin selection marker

<400> SEQUENCE: 14
atgattgaac aagatggatt gcacgcaggt tctccggccg cttgggtgga gaggctattc 60
ggctatgact gggcacaaca gacaatcggc tgctctgatg ccgccgtgtt ccggctgtca 120
gcgcaggggc gcccggttct ttttgtcaag accgacctgt ccggtgccct gaatgaactg 180
caggacgagg cagcgcggct atcgtggctg gccacgacgg gcgttccttg cgcagctgtg 240
ctcgacgttg tcactgaagc gggaagggac tggctgctat tgggcgaagt gccggggcag 300
gatctcctgt catctcacct tgctcctgcc gagaaagtat ccatcatggc tgatgcaatg 360
cggcggctgc atacgcttga tccggctacc tgcccattcg accaccaagc gaaacatcgc 420

```
atcgagcgag cacgtactcg gatggaagcc ggtcttgtcg atcaggatga tctggacgaa    480

gagcatcagg ggctcgcgcc agccgaactg ttcgccaggc tcaaggcgcg catgcccgac    540

ggcgaggatc tcgtcgtgac ccatggcgat gcctgcttgc cgaatatcat ggtggaaaat    600

ggccgctttt ctggattcat cgactgtggc cggctgggtg tggcggaccg ctatcaggac    660

atagcgttgg ctacccgtga tattgctgaa gagcttggcg gcgaatgggc tgaccgcttc    720

ctcgtgcttt acggtatcgc cgctcccgat tcgcagcgca tcgccttcta tcgccttctt    780

gacgagttct tctga                                                      795
```

<210> SEQ ID NO 15
<211> LENGTH: 1677
<212> TYPE: DNA
<213> ORGANISM: Artificial Sequence
<220> FEATURE:
<223> OTHER INFORMATION: GFP-PEST-NEO fusion polypeptide encoding nucleic acid

<400> SEQUENCE: 15

```
atggtgagca agggcgagga gctgttcacc ggggtggtgc ccatcctggt cgagctggac     60

ggcgacgtaa acggccacaa gttcagcgtg tccggcgagg gcgagggcga tgccacctac    120

ggcaagctga ccctgaagtt catctgcacc accggcaagc tgcccgtgcc ctggcccacc    180

ctcgtgacca ccctgaccta cggcgtgcag tgcttcagcc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagca cccagtccgc cctgagcaaa gaccccaacg agaagcgcga tcacatggtc    660

ctgctggagt tcgtgaccgc cgccgggatc actctcggca tggacgagct gtacaagtcc    720

ggactcagat ctcgagctca agcttcgaat tctgcagtcg acggtaccgc gggcccggga    780

tccaccggat ctagacatgg cttcccgccg gaggtggagg agcaggatga tggcacgctg    840

cccatgtctt gtgcccagga gagcgggatg gaccgtagtt taaacattga acaagatgga    900

ttgcacgcag gttctccggc cgcttgggtg gagaggctat tcggctatga ctgggcacaa    960

cagacaatcg gctgctctga tgccgccgtg ttccggctgt cagcgcaggg gcgcccggtt   1020

ctttttgtca agaccgacct gtccggtgcc ctgaatgaac tgcaggacga ggcagcgcgg   1080

ctatcgtggc tggccacgac gggcgttcct tgcgcagctg tgctcgacgt tgtcactgaa   1140

gcgggaaggg actggctgct attgggcgaa gtgccggggc aggatctcct gtcatctcac   1200

cttgctcctg ccgagaaagt atccatcatg gctgatgcaa tgcggcggct gcatacgctt   1260

gatccggcta cctgcccatt cgaccaccaa gcgaaacatc gcatcgagcg agcacgtact   1320

cggatggaag ccggtcttgt cgatcaggat gatctggacg aagagcatca ggggctcgcg   1380

ccagccgaac tgttcgccag gctcaaggcg cgcatgcccg acggcgagga tctcgtcgtg   1440

acccatggcg atgcctgctt gccgaatatc atggtggaaa atggccgctt ttctggattc   1500

atcgactgtg gccggctggg tgtggcggac cgctatcagg acatagcgtt ggctacccgt   1560

gatattgctg aagagcttgg cggcgaatgg gctgaccgct tcctcgtgct ttacggtatc   1620
```

-continued

```
gccgctcccg attcgcagcg catcgccttc tatcgccttc ttgacgagtt cttctga      1677


<210> SEQ ID NO 16
<211> LENGTH: 583
<212> TYPE: DNA
<213> ORGANISM: Encephalomyocarditis virus

<400> SEQUENCE: 16

ggcgcgcccc cctctccctc ccccccccct aacgttactg gccgaagccg cttggaataa     60

ggccggtgtg cgtttgtcta tatgtgattt tccaccatat tgccgtcttt tggcaatgtg    120

agggcccgga aacctggccc tgtcttcttg acgagcattc ctaggggtct ttcccctctc    180

gccaaaggaa tgcaaggtct gttgaatgtc gtgaaggaag cagttcctct ggaagcttct    240

tgaagacaaa caacgtctgt agcgaccctt tgcaggcagc ggaacccccc acctggcgac    300

aggtgcctct gcggccaaaa gccacgtgta taagatacac ctgcaaaggc ggcacaaccc    360

cagtgccacg ttgtgagttg gatagttgtg gaaagagtca aatggctctc ctcaagcgta    420

ttcaacaagg ggctgaagga tgcccagaag gtaccccatt gtatgggatc tgatctgggg    480

cctcggtgca catgctttac atgtgtttag tcgaggttaa aaaaacgtct aggccccccg    540

aaccacgggg acgtggtttt cctttgaaaa acacgatgga tcc                      583


<210> SEQ ID NO 17
<211> LENGTH: 655
<212> TYPE: DNA
<213> ORGANISM: Enterovirus 71

<400> SEQUENCE: 17

ggcgcgcccc cgaagtaact tagaagctgt aaatcaacga tcaatagcag gtgtggcaca     60

ccagtcatac cttgatcaag cacttctgtt tccccggact gagtatcaat aggctgctcg    120

cgcggctgaa ggagaaaacg ttcgttaccc gaccaactac ttcgagaagc ttagtaccac    180

catgaacgag gcagggtgtt tcgctcagca caaccccagt gtagatcagg ctgatgagtc    240

actgcaaccc ccatgggcga ccatggcagt ggctgcgttg gcggcctgcc catggagaaa    300

tccatgggac gctctaattc tgacatggtg tgaagagcct attgagctag ctggtagtcc    360

tccggcccct gaatgcggct aatcctaact gcggagcaca tgctcacaaa ccagtgggtg    420

gtgtgtcgta acgggcaact ctgcagcgga accgactact ttgggtgtcc gtgtttcctt    480

ttattcctat attggctgct tatggtgaca atcaaaaagt tgttaccata tagctattgg    540

attggccatc cggtgtgcaa cagggcaatt gtttacctat ttattggttt tgtaccatta    600

tcactgaagt ctgtgatcac tctcaaattc attttgaccc tcaacacaat caaac         655
```

EXPRESSION VECTOR ORGANIZATION, NOVEL PRODUCTION CELL GENERATION METHODS AND THEIR USE FOR THE RECOMBINANT PRODUCTION OF POLYPEPTIDES

This application is a divisional of U.S. application Ser. No. 14/367,043, filed Jun. 19, 2014, which is a U.S. National Stage Application under 35 U.S.C. § 371 of International Patent Application No. PCT/EP2012/076167, filed on Dec. 19, 2012, which claims the benefit of priority of European Patent Application No. 11195363.4, filed Dec. 22, 2011, the disclosures of each of which are incorporated by reference herein in their entireties.

This application incorporates by reference the Computer Readable Form (CRF) of a Sequence Listing in ASCII text format submitted via EFS-Web. The Sequence Listing text file submitted via EFS-Web, entitled 12279-752-999_SEQ-_LISTING, was created on Apr. 3, 2018, and is 22,252 bytes in size.

Herein are reported novel vector organizations, novel methods for the generation of production cell lines, such as novel transfection or selection methods, as well as the use of these expression vectors and production cell lines for the recombinant production of polypeptides of interest.

BACKGROUND OF THE INVENTION

The transcription level of a gene can have a strong influence on its expression level and therefore determines the productivity of a cell. It is mainly influenced by three vector elements: by the promoter, the polyA signal sequence and (if present) by a transcription terminator.

The nucleic acid encoding an antibody heavy chain generally comprises a leader sequence (a signal sequence) (approximately 57 bp/19 aa), which is removed upon maturation of the protein, a variable region, VH (approximately 350 bp/115 aa), and the constant region, CH (approximately 990 bp/330 aa). The nucleic acid encoding an antibody light chain is generally composed of a leader sequence (approximately 66 bp/22 aa) which is removed upon maturation of the protein, a variable region, VK or VL (approximately 350 bp/115 aa), and a constant region, CK or CL (approximately 321 bp/107 aa).

The recombinant production of antibodies in eukaryotic cells involves the creation of expression systems (see, McCafferty, J., et al., (eds.), Antibody Engineering, A Practical Approach, IRL Press (1997)). For development of antibody expression systems an expression cassette comprising a light chain encoding nucleic acid flanked by a promoter and a poly-adenylation (polyA) region is created. Also, a heavy chain expression cassette comprising a heavy chain encoding nucleic acid flanked by a promoter and a polyA region is created. The expression cassette of the heavy chain may be combined into the light chain expression cassette in a single vector containing both heavy and light chain expression cassettes or may be integrated in two separate vectors.

Immunoglobulin DNA cassette molecules, monobody constructs, methods of production, and methods of use therefor are reported in U.S. Pat. No. 7,053,202. In U.S. Pat. No. 5,168,062 transfer vectors and microorganisms containing human cytomegalovirus immediate-early promoter-regulatory DNA sequence are reported.

A DNA fragment containing a promoter region for human polypeptide chain elongation factor-1α, its base sequence and expression plasmids containing the DNA fragment having high applicability to a wide range of host cells with high expression capacity is reported in U.S. Pat. No. 5,225,348. In U.S. Pat. No. 5,266,491 expression plasmids containing SV40 replication origin and a DNA fragment having a promoter region for a human polypeptide chain elongation factor-1a gene are reported. Recombinant DNA compounds and the expression of polypeptides such as tPA are reported in U.S. Pat. No. 5,122,458. In U.S. Pat. No. 7,422,874 an expression vector for animal cell is reported.

Kim, D., et al. report improved mammalian cell expression systems by manipulating transcriptional termination regions (Biotechnol. Prog. 19 (2003) 1620-1622). That a 9-nt segment of a cellular mRNA can function as an internal ribosome entry site (IRES) and when present in linked multiple copies greatly enhances IRES activity is reported by Chappell, S. A., et al. (Proc. Natl. Acad. Sci. USA 97 (2000) 1536-1541. Corish, P. and Tyler-Smith, C., report the attenuation of green fluorescent protein half-life in mammalian cells (Prot. Eng. 12 (1999) 1035-1040). A novel GFPneo vector designed for the isolation and analysis of enhancer elements in transfected mammalian cells is reported by Primig, M., et al. (Gene 215 (1998) 181-189). Ng, S. K., et al. report the application of destabilizing sequences on selection marker for improved recombinant protein productivity in CHO-DG44 (Metabol. Eng. 9 (2007) 304-316).

Sanna Pietro, P., reports the expression of antibody Fab fragments and whole immunoglobulin in mammalian cells (Meth. Mol. Biol. 178 (2002) 389-395). A cell display library for gene cloning of variable regions of human antibodies to hepatitis B surface antigen is reported by Higuchi, K., et al. (J. Immunol. Meth. 202 (1997) 193-204). Kim, D., et al., report improved mammalian expression systems by manipulating transcriptional termination regions (Biotechnol. Progress 19 (2003) 1620-1622). Guidelines to cell engineering for monoclonal antibody production are reported by Costa, R. A., et al. (Eur. J. Pharmaceut. Biopharmaceut. 74 (2010) 127-138). Kim, D. W., et al., report the use of the human elongation factor 1 alpha promoter as a versatile and efficient expression system (Gene 91 (1990) 217-223). Comparison of intron-dependent and intron independent gene expression is reported by Buchman, A. R., et al., (Mol. Cell. Biol. 8 (1988) 4395-4405). Wang, F., et al., report antibody expression in mammalian cells (in Therapeutic monoclonal antibodies—From bench to clinic, Wiley (2009) pages 557-572). A comparative study of different vector designs for the mammalian expression of recombinant IgG antibodies is reported by Li et al. (J. Immunol. Meth. 318 (2007) 113-124). Ho, S. C. L., et al. report "IRES-mediated tricistronic vectors for enhancing generation of high monoclonal antibody expressing CHO cell lines (J. Biotechnol. 157 (2011) 130-139). Production of anti-CD2 chimeric antibody by recombinant animal cells is reported by Hotta, A., et al. (J. Biosci. Bioeng. 98 (2004) 298-303). Lee, J-C., et al. report "High-efficiency protein expression mediated by enterovirus 71 internal ribosome entry (Biotechnol. Bioeng. 90 (2005) 656-662). In WO 2008/142124 recombinant protein production in Avian EBX® cells is reported.

SUMMARY OF THE INVENTION

It has been found that for the recombinant production of antibodies the position of the heavy chain expression cassette in front of the light chain expression cassette (HC-LC (5'-3')) provides for better expression results compared to the inverse order (LC-HC (5'-3')). Additionally it has been found that the position of the selection marker after both antibody chain expression cassettes provides for better expression results (HC-LC-SM (5'-3')) compared to the bidirectional position in front of the first antibody chain (SM (3'-5')-HC-LC (5'-3')).

It has been found that for stable transfections the in row arrangement of 1) antibody heavy chain, 2) antibody light chain and 3) selection marker has shown to be optimal. But whereas the hEF1α promoter is clearly superior to the hCMV promoter in stable pools, we have seen the clear opposite effect on single clone level. Here, the human cytomegalovirus immediate early promoter/enhancer (hCMV) generated clones with highest productivity. Moreover, its performance can further be improved by combining it with the bGH polyA signal and the terminator sequence of the human gastrin gene (hGT), which increases both productivity and stability of expression.

It has been found that the use of an expression vector comprising an expression cassettes for an antibody heavy chain and an expression cassette for an antibody light chain each comprising a promoter, a structural gene and a polyA signal sequence and optionally a terminator sequence, results in a higher number of antibody producing/secreting cell clones after transfection if 1) the promoter is the human cytomegalovirus promoter (hCMV), the polyA signal sequence is the bovine growth hormone polyA signal sequence (bGH polyA) and the terminator sequence is the human gastrin gene transcription terminator sequence (hGT), or 2) the promoter is the human elongation factor 1 alpha promoter (EF1 alpha), the polyA signal sequence is the bovine growth hormone polyA signal sequence (bGH polyA) and the terminator sequence is absent.

By using an expression vector as outlined above a higher number of antibody producing/secreting cells can be obtained after transfection and, thus, the required efforts to identify a high producer cell suitable for large scale recombinant antibody production are reduced.

One aspect as reported herein is an expression vector comprising

- an antibody light chain expression cassette,
- an antibody heavy chain expression cassette, and
- a selection marker expression cassette,
- wherein the expression cassettes are arranged unidirectional, and
- wherein the expression cassettes are arranged in the 5' to 3' sequence of antibody heavy chain expression cassette, antibody light chain expression cassette and selection marker expression cassette.

In one embodiment the antibody light chain expression cassette and/or the antibody heavy chain expression cassette and/or the selection marker cassette comprise independently of each other comprise a promoter selected from the human elongation factor 1 alpha promoter, the human CMV promoter, and the SV40 promoter.

In one embodiment one, two, or all three expression cassettes comprise the human elongation factor 1 alpha promoter. In one embodiment the antibody light chain expression cassette and/or the antibody heavy chain expression cassette and/or the selection marker cassette comprise independently of each other the human elongation factor 1 alpha promoter. In one embodiment the expression cassette does not comprise a terminator sequence, i.e. the expression cassette is free of a terminator sequence. In one embodiment the terminator sequence is the human gastrin gene transcription terminator sequence (hGT).

In one embodiment one, two, or all three expression cassettes comprise the human CMV promoter. In one embodiment the antibody light chain expression cassette and/or the antibody heavy chain expression cassette and/or the selection marker cassette comprise independently of each other the human CMV promoter.

In one embodiment one, two, or three expression cassettes comprise the bovine growth hormone polyA signal sequence. In one embodiment the antibody light chain expression cassette and/or the antibody heavy chain expression cassette and/or the selection marker cassette comprise independently of each other the bovine growth hormone polyA signal sequence.

In one embodiment the antibody light chain expression cassette and/or the antibody heavy chain expression cassette and/or the selection marker cassette comprise independently of each other a polyA signal sequence selected from the bovine growth hormone polyA signal sequence and the SV40 polyA signal sequence.

In one embodiment one, two, or all three expression cassettes comprise the human gastrin terminator sequence after the polyA signal sequence with the proviso that the expression cassettes do not comprise the human elongation factor 1 alpha promoter. In one embodiment the antibody light chain expression cassette and/or the antibody heavy chain expression cassette and/or the selection marker cassette comprise independently of each other the human gastrin terminator sequence after the polyA signal sequence.

In one embodiment the antibody light chain expression cassette and/or the antibody heavy chain expression cassette and/or the selection marker cassette comprise independently of each other in 5' to 3' direction the bovine growth hormone polyA signal sequence and the human gastrin terminator sequence with the proviso that the expression cassettes do not comprise the human elongation factor 1 alpha promoter.

In one embodiment the promoter of one, two, or all three expression cassettes comprises an Intron A.

In one embodiment one, two, or all three expression cassettes comprise the SV40 polyA signal sequence.

In one embodiment one, two, or all three expression cassettes comprise the SV40 promoter.

In one embodiment the nucleic acid encoding the antibody light chain and/or the nucleic acid encoding the antibody heavy chain comprises at least one intron.

In one embodiment the nucleic acid encoding the antibody light chain and/or the nucleic acid encoding the antibody heavy chain is cDNA.

One aspect as reported herein is the use of an expression vector as reported herein for the recombinant production of an antibody.

One aspect as reported herein is the use of an expression vector as reported herein for the generation of a stable cell line.

One aspect as reported herein is the use of an expression vector as reported herein for the generation of a production cell line.

One aspect as reported herein is the use of an expression vector as reported herein comprising at least one expression cassette comprising a human elongation factor 1 alpha promoter for the generation of a stable cell line.

One aspect as reported herein is the use of an expression vector as reported herein comprising at least one expression cassette comprising a human elongation factor 1 alpha promoter for the generation of a production cell line.

One aspect as reported herein is the use of an expression vector as reported herein comprising at least one expression cassette comprising a human elongation factor 1 alpha promoter for the recombinant production of an antibody.

One aspect as reported herein is the use of an expression vector as reported herein comprising at least one expression cassette comprising a human CMV promoter for the generation of a production cell line.

One aspect as reported herein is the use of an expression vector as reported herein comprising at least one expression cassette comprising a human CMV promoter for the generation of a stable cell line.

One aspect as reported herein is the use of an expression vector as reported herein comprising at least one expression cassette comprising a human CMV promoter for the production of an antibody.

One aspect as reported herein is a method for the transfection of a eukaryotic cell with an expression vector, characterized in that the expression vector is linearized prior to the transfection by cleavage in the prokaryotic origin of replication.

In one embodiment the prokaryotic origin of replication is between one antibody light chain expression cassette and one antibody heavy chain expression cassette.

One aspect as reported herein is the use of a method as reported herein for the generation of a eukaryotic cell for the recombinant production of an antibody.

One aspect as reported herein is a method for the selection of a eukaryotic cell comprising a nucleic acid encoding an antibody, characterized in that the selection agent is added to the cultivation medium for the first time about 24 hours after transfection.

One aspect as reported herein is the use of a method as reported herein for the generation of a eukaryotic cell for the recombinant production of an antibody.

One aspect as reported herein is the use of a cell selected with a method as reported herein for the recombinant production of an antibody.

One aspect as reported herein is a method for the production of an antibody comprising the following steps:

- cultivating a eukaryotic cell comprising an expression vector as reported herein, and
- recovering the antibody from the cell or the cultivation medium.

One aspect as reported herein is a method for the production of an antibody comprising the following step:

- cultivating a eukaryotic cell, which has been obtained by the transfection with an expression vector that has been linearized prior to the transfection by cleavage in the prokaryotic origin of replication, and
- recovering the antibody from the cell or the cultivation medium.

One aspect as reported herein is a method for the production of an antibody comprising the following step:

- cultivating a eukaryotic cell, which has been selected by the addition of a selection agent about 24 hours after transfection to the cultivation, and
- recovering the antibody from the cell or the cultivation medium.

One aspect as reported herein is a method for the transfection of a eukaryotic cell with an expression vector comprising prokaryotic and eukaryotic nucleic acid sequences, characterized in that the prokaryotic nucleic acid sequences are removed from the expression vector prior to the transfection of the eukaryotic cell with the expression vector.

One aspect as reported herein is the use of a linearized expression vector comprising no prokaryotic nucleic acid sequences for the transfection of a eukaryotic cell.

One aspect as reported herein is the use of an expression vector comprising only eukaryotic nucleic acid sequences for the generation of a eukaryotic cell for the recombinant production of an antibody.

In one embodiment of all aspects as reported herein the antibody is a bispecific antibody.

In one embodiment the bispecific antibody has a first binding specificity or binding site that specifically binds to a first antigen or a first epitope on an antigen and the bispecific antibody has a second binding specificity or binding site that specifically binds to a second antigen or second epitope on the antigen.

If one embodiment the expression vector comprises either

- a first expression cassette comprising in 5' to 3' direction a promoter, a nucleic acid encoding a first antibody light chain, a polyA signal sequence, and optionally a terminator sequence,
- a second expression cassette comprising in 5' to 3' direction a promoter, a nucleic acid encoding a second antibody light chain, a polyA signal sequence, and optionally a terminator sequence,
- a third expression cassette comprising in 5' to 3' direction a promoter, a nucleic acid encoding a first antibody heavy chain, a polyA signal sequence, and optionally a terminator sequence,
- a fourth expression cassette comprising in 5' to 3' direction a promoter, a nucleic acid encoding a second antibody heavy chain, a polyA signal sequence, and optionally a terminator sequence, or

- a first expression cassette comprising in 5' to 3' direction a promoter, a nucleic acid encoding an antibody light chain, a polyA signal sequence, and optionally a terminator sequence,
- a second expression cassette comprising in 5' to 3' direction a promoter, a nucleic acid encoding a first antibody heavy chain, a polyA signal sequence, and optionally a terminator sequence, and
- a third expression cassette comprising in 5' to 3' direction a promoter, a nucleic acid encoding a second antibody heavy chain, a polyA signal sequence, and optionally a terminator sequence,
- whereby the antibody light chain is a common light chain for both antibody heavy chains.

In one embodiment of all aspects as reported herein the expression vector comprises

- an antibody light chain expression cassette,
- a first antibody heavy chain expression cassette,
- a second antibody heavy chain expression cassette, and
- a selection marker expression cassette,
- wherein at least one of the antibody heavy chain expression cassettes, the antibody light chain expression cassette, and the selection marker expression cassette are arranged unidirectional, and
- wherein the unidirectional expression cassettes are arranged in the 5' to 3' sequence of antibody heavy chain expression cassette, antibody light chain expression cassette and selection marker expression cassette.

In one embodiment of all aspects as reported herein the expression vector comprises

- a first antibody light chain expression cassette,
- a second antibody light chain expression cassette,
- a first antibody heavy chain expression cassette,
- a second antibody heavy chain expression cassette, and
- a selection marker expression cassette,
- wherein one of the antibody heavy chain expression cassettes, one of the antibody light chain expression cassette, and the selection marker expression cassette are arranged unidirectional, and
- wherein the unidirectional expression cassettes are arranged in the 5' to 3' sequence of antibody heavy chain expression cassette, antibody light chain expression cassette and selection marker expression cassette.

In one embodiment encodes the one of the antibody heavy chain expression cassettes an antibody heavy chain comprising a hole mutation.

In one embodiment encodes one of the antibody heavy chain expression cassettes an antibody heavy chain comprising a knob mutation.

In one embodiment encodes one of the antibody light chain expression cassettes an antibody light chain comprising an antibody light chain variable domain and an antibody heavy chain CH1 domain as constant domain and/or one of the antibody light chain expression cassettes an antibody light chain comprising an antibody light chain variable domain and an antibody light chain CL domain as constant domain.

In one embodiment one of the antibody heavy chain expression cassettes encodes an antibody heavy chain comprising as first constant domain an antibody light chain constant domain (CL), and/or one of the antibody heavy chain expression cassettes encodes an antibody heavy chain comprising as first constant domain an antibody heavy chain CH1 domain.

In one embodiment the hCMV promoter has the sequence of SEQ ID NO: 01. This is the hCMV promoter without Intron A and without 5'UTR.

In one embodiment the hCMV promoter has the sequence of SEQ ID NO: 02. This is the hCMV promoter without Intron A and with 5'UTR.

In one embodiment the hCMV promoter has the sequence of SEQ ID NO: 03. This is the full length hCMV promoter with Intron A.

In one embodiment the human elongation factor 1 alpha promoter has the sequence of SEQ ID NO: 04. This is the hEF1 alpha promoter without Intron A.

In one embodiment the human elongation factor 1 alpha promoter has the sequence of SEQ ID NO: 05. This is the hEF1 alpha promoter with Intron A.

In one embodiment the human elongation factor 1 alpha promoter has the sequence of SEQ ID NO: 06. This is a short hEF1 alpha promoter with Intron A and with 5'UTR.

In one embodiment the rat CMV promoter has the sequence of SEQ ID NO: 07.

In one embodiment the SV40 polyA signal sequence has the sequence of SEQ ID NO: 08.

In one embodiment the bovine growth hormone polyA signal sequence has the sequence SEQ ID NO: 09.

In one embodiment the human gastrin terminator has the sequence of SEQ ID NO: 10.

In one embodiment the SV40 promoter has the sequence of SEQ ID NO: 11.

In one embodiment the PEST sequence of ornithine decarboxylase is encoded by the sequence of SEQ ID NO: 12.

In one embodiment the GFP sequence is encoded by the sequence of SEQ ID NO: 13.

In one embodiment the neomycin selection marker has the sequence of SEQ ID NO: 14.

In one embodiment the GFP-PEST-NEO fusion polypeptide is encoded by the sequence of SEQ ID NO: 15.

In one embodiment the EMCV-IRES has the sequence of SEQ ID NO: 16.

In one embodiment the EV71-IRES has the sequence of SEQ ID NO: 17.

DETAILED DESCRIPTION OF THE INVENTION

I. General Aspects

As known to a person skilled in the art enables the use of recombinant DNA technology the production of numerous derivatives of a nucleic acid and/or polypeptide. Such derivatives can, for example, be modified in one individual or several positions by substitution, alteration, exchange, deletion, or insertion. The modification or derivatization can, for example, be carried out by means of site directed mutagenesis. Such modifications can easily be carried out by a person skilled in the art (see e.g. Sambrook, J., et al., Molecular Cloning: A Laboratory Manual, Cold Spring Harbor Laboratory Press, New York, USA (1999)). The use of recombinant technology enables a person skilled in the art to transform various host cells with heterologous nucleic acid(s). Although the transcription and translation, i.e. expression, machinery of different cells use the same elements, cells belonging to different species may have among other things a different so-called codon usage. Thereby identical polypeptides (with respect to amino acid sequence) may be encoded by different nucleic acid(s). Also, due to the degeneracy of the genetic code, different nucleic acids may encode the same polypeptide.

The use of recombinant DNA technology enables the production of numerous derivatives of a nucleic acid and/or polypeptide. Such derivatives can, for example, be modified in one individual or several positions by substitution, alteration, exchange, deletion, or insertion. The modification or derivatization can, for example, be carried out by means of site directed mutagenesis. Such modifications can easily be carried out by a person skilled in the art (see e.g. Sambrook, J., et al., Molecular Cloning: A Laboratory Manual, Cold Spring Harbor Laboratory Press, New York, USA (1999); Hames, B. D., and Higgins, S. J., Nucleic acid hybridization—a practical approach, IRL Press, Oxford, England (1985)).

The use of recombinant technology enables the transformation of various host cells with heterologous nucleic acid(s). Although the transcription and translation, i.e. expression, machinery of different cells use the same elements, cells belonging to different species may have among other things a different so-called codon usage.

Thereby identical polypeptides (with respect to amino acid sequence) may be encoded by different nucleic acid(s). Also, due to the degeneracy of the genetic code, different nucleic acids may encode the same polypeptide.

Definitions

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "expression" as used herein refers to transcription and/or translation processes occurring within a cell. The level of transcription of a nucleic acid sequence of interest in a cell can be determined on the basis of the amount of corresponding mRNA that is present in the cell. For example, mRNA transcribed from a sequence of interest can be quantitated by RT-PCR or by Northern hybridization (see Sambrook et al., 1999, supra). Polypeptides encoded by a nucleic acid of interest can be quantitated by various methods, e.g. by ELISA, by assaying for the biological activity of the polypeptide, or by employing assays that are independent of such activity, such as Western blotting or radioimmunoassay, using immunoglobulins that recognize and bind to the polypeptide (see Sambrook et al., 1999, supra).

An "expression cassette" refers to a construct that contains the necessary regulatory elements, such as promoter and polyadenylation site, for expression of at least the contained nucleic acid in a cell.

An "expression vector" is a nucleic acid providing all required elements for the expression of the comprised structural gene(s) in a host cell. Typically, an expression plasmid comprises a prokaryotic plasmid propagation unit, e.g. for *E. coli*, comprising an origin of replication, and a selectable marker, an eukaryotic selection marker, and one or more expression cassettes for the expression of the structural gene(s) of interest each comprising a promoter, a structural gene, and a transcription terminator including a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A., et al., Sequences of Proteins of Immunological Interest, 5th ed., Public Health Service, National Institutes of Health, Bethesda, Md. (1991), NIH Publication 91-3242.

An "Fc-region" is a term well known and defined on basis of the papain cleavage of an antibody heavy chain. The complexes as reported herein may comprise in one embodiment as antibody heavy chain hinge region polypeptide a human Fc-region or an Fc-region derived from human origin. In a further embodiment the Fc-region is either an Fc-region of a human antibody of the subclass IgG4 or an Fc-region of a human antibody of the subclass IgG1, IgG2, or IgG3, which is modified in such a way that no Fcγ receptor (e.g. FcγRIIIa) binding and/or no C1 q binding can be detected. In one embodiment the Fc-region is a human Fc-region and especially either from human IgG4 subclass or a mutated Fc-region from human IgG1 subclass. In one embodiment the Fc-region is from human IgG1 subclass with mutations L234A and L235A. While IgG4 shows reduced Fcγ receptor (FcγRIIIa) binding, antibodies of other IgG subclasses show strong binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, or/and His435 are residues which, if altered, provide also reduced Fcγ receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434). In one embodiment the antibody to be expressed in an aspect as reported herein is in regard to Fcγ receptor binding of IgG4 subclass or of IgG1 or IgG2 subclass, with a mutation in L234, L235, and/or D265, and/or contains the PVA236 mutation. In one embodiment the mutations are S228P, L234A, L235A, L235E, and/or PVA236 (PVA236 denotes that the amino acid sequence ELLG (given in one letter amino acid code) from amino acid position 233 to 236 of IgG1 or EFLG of IgG4 is replaced by PVA). In one embodiment the mutations are S228P of IgG4, and L234A and L235A of IgG1. The Fc-region of an antibody is directly involved in ADCC (antibody-dependent cell-mediated cytotoxicity) and CDC (complement-dependent cytotoxicity). A complex which does not bind Fcγ receptor and/or complement factor C1q does not elicit antibody-dependent cellular cytotoxicity (ADCC) and/or complement dependent cytotoxicity (CDC). The knob modification denotes the mutation T366W in the CH3 domain of an antibody (numbering according to Kabat). The hole-modification denotes the mutations T366S, L368A and Y407V in the CH3 domain of an antibody. In addition to the knob and hole modification the mutation S354C in the one CH3 domain and the mutation Y349C in the other CH3 domain can be present.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody", "intact antibody", and "whole antibody" are used herein interchangeably to refer to an antibody having a structure substantially similar to a native antibody structure or having heavy chains that contain an Fc-region as defined herein.

A "gene" denotes a nucleic acid which is a segment e.g. on a chromosome or on a plasmid which can affect the expression of a peptide, polypeptide, or protein. Beside the coding region, i.e. the structural gene, a gene comprises other functional elements e.g. a signal sequence, promoter(s), introns, and/or terminators.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat, E. A., et al., Sequences of Proteins of Immunological Interest, 5th ed. Public Health Service, National Institutes of Health, Bethesda, Md. (1991), NIH Publication 91-3242). With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3 (Almagro, J. C. and Fransson, J., Front. Biosci. 13 (2008) 1619-1633). Unless otherwise indicated, HVR residues and other residues in the variable domain (e.g., FR residues) are numbered herein according to Kabat et al., supra.

An "internal ribosome entry site" or "IRES" describes a sequence which functionally promotes translation initiation independent from the gene 5' of the-IRES and allows two cistrons (open reading frames) to be translated from a single transcript in an animal cell. The-IRES provides an independent ribosome entry site for translation of the open reading frame immediately downstream (downstream is used interchangeably herein with 3') of it. Unlike bacterial mRNA which can be polycistronic, i.e. encode several different polypeptides that are translated sequentially from the mRNAs, most mRNAs of animal cells are monocistronic and code for the synthesis of only one protein. With a polycistronic transcript in a eukaryotic cell, translation would initiate from the 5' most translation initiation site, terminate at the first stop codon, and the transcript would be released from the ribosome, resulting in the translation of only the first encoded polypeptide in the mRNA. In a eukaryotic cell, a polycistronic transcript having an-IRES operably linked to the second or subsequent open reading frame in the transcript allows the sequential translation of that downstream open reading frame to produce the two or more polypeptides encoded by the same transcript. The use of-IRES elements in vector construction has been previously described, see, e.g., Pelletier, J., et al., Nature 334 (1988) 320-325; Jang, S. K., et al., J. Virol. 63 (1989) 1651-1660; Davies, M. V., et al., J. Virol. 66 (1992) 1924-1932; Adam, M. A., et al., J. Virol. 65 (1991) 4985-4990; Morgan, R. A., et al., Nucl. Acids Res. 20 (1992) 1293-1299; Sugimoto, Y., et al., Biotechnology 12 (1994) 694-698; Ramesh, N., et al., Nucl. Acids Res. 24 (1996) 2697-2700; and Mosser, D. D., et al., BioTechniques 22 (1997) 150-152).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "nucleic acid" as used herein, refers to a polymeric molecule consisting of individual nucleotides (also called bases) a, c, g, and t (or u in RNA), for example to DNA, RNA, or modifications thereof. This polynucleotide molecule can be a naturally occurring polynucleotide molecule or a synthetic polynucleotide molecule or a combination of one or more naturally occurring polynucleotide molecules with one or more synthetic polynucleotide molecules. Also encompassed by this definition are naturally occurring polynucleotide molecules in which one or more nucleotides are changed (e.g. by mutagenesis), deleted, or added. A nucleic acid can either be isolated, or integrated in another nucleic acid, e.g. in an expression cassette, a plasmid, or the chromosome of a host cell. A nucleic acid is likewise characterized by its nucleic acid sequence consisting of individual nucleotides.

To a person skilled in the art procedures and methods are well known to convert an amino acid sequence, e.g. of a polypeptide, into a corresponding nucleic acid sequence encoding this amino acid sequence. Therefore, a nucleic acid is characterized by its nucleic acid sequence consisting of individual nucleotides and likewise by the amino acid sequence of a polypeptide encoded thereby.

A "nucleic acid" as used herein, also refers to a naturally occurring or partially or fully non-naturally occurring nucleic acid encoding a polypeptide which can be produced recombinantly. The nucleic acid can be build up of DNA-fragments which are either isolated or synthesized by chemical means. The nucleic acid can be integrated into another nucleic acid, e.g. in an expression plasmid or the genome/chromosome of a eukaryotic host cell. Plasmid includes shuttle and expression plasmids. Typically, the plasmid will also comprise a prokaryotic propagation unit comprising an origin of replication (e.g. the ColE1 origin of replication) and a selectable marker (e.g. ampicillin or tetracycline resistance gene), for replication and selection, respectively, of the plasmid in prokaryotes.

"Operably linked" refers to a juxtaposition of two or more components, wherein the components so described are in a relationship permitting them to function in their intended manner. For example, a promoter and/or enhancer are operably linked to a coding sequence, if it acts in cis to control or modulate transcription of the linked sequence. Generally, but not necessarily, the DNA sequences that are "operably linked" are contiguous and, where necessary to join two protein encoding regions such as a secretory leader and a polypeptide, contiguous and in (reading) frame. However, although an operably linked promoter is generally located upstream of the coding sequence, it is not necessarily contiguous with it. Enhancers do not have to be contiguous. An enhancer is operably linked to a coding sequence if the enhancer increases transcription of the coding sequence. Operably linked enhancers can be located upstream, within or downstream of coding sequences and at considerable distance from the promoter. A polyadenylation site is operably linked to a coding sequence if it is located at the downstream end of the coding sequence such that transcription proceeds through the coding sequence into the polyadenylation sequence. A translation stop codon is operably linked to an exonic nucleic acid sequence if it is located at the downstream end (3' end) of the coding sequence such that translation proceeds through the coding sequence to the stop codon and is terminated there. Linking is accomplished by recombinant methods known in the art, e.g., using PCR methodology and/or by ligation at convenient restriction sites. If convenient restriction sites do not exist, then synthetic oligonucleotide adaptors or linkers are used in accord with conventional practice.

A "polycistronic transcription unit" is a transcription unit in which more than one structural gene is under the control of the same promoter.

The term "polyadenylation signal" (polyA signal) as used within this application denotes a nucleic acid sequence used to induce cleavage and polyadenylation of primary transcripts of a specific nucleic acid sequence segment. The 3' untranslated region comprising a polyadenylation signal can be selected from the group consisting of the 3' untranslated region comprising a polyadenylation signals derived from SV40, the gene for bovine growth hormone (bGH), immunoglobulin genes, and the thymidine kinase gene (tk, e.g. Herpes Simplex thymidine kinase polyadenylation signal).

A "promoter" refers to a polynucleotide sequence that controls transcription of a gene/structural gene or nucleic acid sequence to which it is operably linked. A promoter includes signals for RNA polymerase binding and transcription initiation. The promoters used will be functional in the cell type of the host cell in which expression of the selected sequence is contemplated. A large number of promoters including constitutive, inducible and repressible promoters from a variety of different sources, are well known in the art (and identified in databases such as GenBank) and are available as or within cloned polynucleotides (from, e.g., depositories such as ATCC as well as other commercial or individual sources).

A "promoter" comprises a nucleotide sequence that directs the transcription of a structural gene. Typically, a promoter is located in the 5' non-coding or untranslated region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee, R. E., et al., Mol. Endocrinol. 7 (1993) 551), cyclic AMP response elements (CREs), serum response elements (SREs; Treisman, R., Seminars in Cancer Biol. 1 (1990) 47), glucocorticoid response elements (GREs), and binding sites for other transcription factors, such as CRE/ATF (O'Reilly, M. A., et al., J. Biol. Chem. 267 (1992) 19938), AP2 (Ye, J., et al., J. Biol. Chem. 269 (1994) 25728), SP1, cAMP response element binding protein (CREB; Loeken, M. R., Gene Expr. 3 (1993) 253) and octamer factors (see, in general, Watson et al., (eds.), Molecular Biology of the Gene, 4th ed. (The Benjamin/Cummings Publishing Company, Inc. (1987)), and Lemaigre, F. P. and Rousseau, G. G., Biochem. J. 303 (1994) 1-14). If a promoter is an inducible promoter, then the rate of transcription increases in response to an inducing agent. In contrast, the rate of transcription is not regulated by an inducing agent if the promoter is a constitutive promoter. Repressible promoters are also known. For example, the c-fos promoter is specifically activated upon binding of growth hormone to its receptor on the cell surface. Tetracycline (tet) regulated expression can be achieved by artificial hybrid promoters that consist e.g. of a CMV promoter followed by two Tet-operator sites. The Tet-repressor binds to the two Tet-operator sites and blocks transcription. Upon addition of the inducer tetracycline, Tet-repressor is released from the Tet-operator sites and transcription proceeds (Gossen, M. and Bujard, H. PNAS 89 (1992) 5547-5551). For other inducible promoters including metallothionein and heat shock promoters, see, e.g., Sambrook et al. (supra) and Gossen et al., Curr. Opin. Biotech. 5 (1994) 516-520. Among the eukaryotic promoters that have been identified as strong promoters for high-level expression are the SV40 early promoter, adenovirus major late promoter, mouse metallothionein-I promoter, Rous sarcoma virus long terminal repeat, Chinese hamster elongation factor 1 alpha (CHEF-1, see e.g. U.S. Pat. No. 5,888,809), human EF-1 alpha, ubiquitin, and human cytomegalovirus immediate early promoter (CMV IE).

The "promoter" can be constitutive or inducible. An enhancer (i.e., a cis-acting DNA element that acts on a promoter to increase transcription) may be necessary to function in conjunction with the promoter to increase the level of expression obtained with a promoter alone, and may be included as a transcriptional regulatory element. Often, the polynucleotide segment containing the promoter will include enhancer sequences as well (e.g., CMV or SV40).

The terms "stably transformed", "stable transfected", or "stable" as used within this application denotes a heritable and stable integration of exogenous nucleic acid into a host cell genome/chromosome. A stable transfected cell is obtained after a cell selection process under selective growth conditions, i.e. in the presence of one or more selection markers.

A "structural gene" denotes the region of a gene without a signal sequence, i.e. the coding region.

The term "transcription terminator" denotes a DNA sequence of 50-750 base pairs in length which gives the RNA polymerase the signal for termination of the mRNA synthesis. Very efficient (strong) terminators at the 3' end of an expression cassette are advisable to prevent the RNA polymerase from reading through particularly when using strong promoters. Inefficient transcription terminators can lead to the formation of an operon-like mRNA which can be the reason for an undesired, e.g. plasmid-coded, gene expression.

Within the scope of the present invention, transfected cells may be obtained with substantially any kind of transfection method known in the art. For example, the nucleic acid may be introduced into the cells by means of electroporation or microinjection. Alternatively, lipofection reagents such as FuGENE 6 (Roche Diagnostics GmbH, Germany), X-tremeGENE (Roche Diagnostics GmbH, Germany), and LipofectAmine (Invitrogen Corp., USA) may be used. Still alternatively, the nucleic acid may be introduced into the cell by appropriate viral vector systems based on retroviruses, lentiviruses, adenoviruses, or adeno-associated viruses (Singer, O., Proc. Natl. Acad. Sci. USA 101 (2004) 5313-5314).

The term "transient transfection" as used within this application denotes a process in which the nucleic acid introduced into a cell does not integrate into the genome or chromosomal DNA of that cell. It is in fact maintained as an extrachromosomal element, e.g. as an episome, in the cell. Transcription processes of the nucleic acid of the episome are not affected and e.g. a protein encoded by the nucleic acid of the episome is produced. A transient transfection results in a "transient transfected" cell.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs) (see, e.g., Kindt, T. J., et al., Kuby Immunology, 6th ed., W.H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S., et al., J. Immunol. 150 (1993) 880-887; Clackson, T., et al., Nature 352 (1991) 624-628).

The term "vector" as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

Antibody

The methods and compositions provided herein are for the production of recombinant monoclonal antibodies. An antibody can be of various structures, such as but not limited to monospecific antibodies, multispecific antibodies (e.g., bispecific antibodies), antibody fragments, monovalent antibodies, multivalent antibodies (e.g. bivalent antibodies).

In certain embodiments, the antibody is an antibody fragment. Antibody fragments include, but are not limited to, Fab, Fab', Fab'-SH, $F(ab')_2$, Fv, and scFv fragments, and other fragments described below. For a review of certain antibody fragments, see Hudson, P. J., et al., Nat. Med. 9 (2003) 129-134. For a review of scFv fragments, see, e.g., Plueckthun, A., In: The Pharmacology of Monoclonal Antibodies, Vol. 113, Rosenburg and Moore (eds.), Springer-Verlag, New York (1994), pp. 269-315; see also WO 1993/16185; and U.S. Pat. Nos. 5,571,894 and 5,587,458. For discussion of Fab and $F(ab')_2$ fragments comprising salvage receptor binding epitope residues and having increased in vivo half-life, see U.S. Pat. No. 5,869,046.

Diabodies are antibody fragments with two antigen-binding sites that may be bivalent or bispecific (see, for example, EP 0 404 097; WO 1993/01161; Hudson, P. J., et al., Nat. Med. 9 (2003) 129-134; and Holliger, P., et al., Proc. Natl. Acad. Sci. USA 90 (1993) 6444-6448). Triabodies and tetrabodies are also described in Hudson, P. J., et al., Nat. Med. 9 (2003) 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. *E. coli* or phage), as described herein.

In certain embodiments, the antibody is a chimeric antibody. Certain chimeric antibodies are described, e.g., in U.S. Pat. No. 4,816,567; and Morrison, S. L., et al., Proc. Natl. Acad. Sci. USA 81 (1984) 6851-6855. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front. Biosci. 13 (2008) 1619-1633, and are further described, e.g., in Riechmann, I., et al., Nature 332 (1988) 323-329; Queen, C., et al., Proc. Natl. Acad. Sci. USA 86 (1989) 10029-10033; U.S. Pat. Nos. 5,821,337, 7,527,791, 6,982,321, and 7,087,409; Kashmiri, S. V., et al., Methods 36 (2005) 25-34 (describing SDR (a-CDR) grafting); Padlan, E. A., Mol.

Immunol. 28 (1991) 489-498 (describing "resurfacing"); Dall' Acqua, W. F., et al., Methods 36 (2005) 43-60 (describing "FR shuffling"); and Osbourn, J., et al., Methods 36 (2005) 61-68 and Klimka, A., et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J., et al., J. Immunol. 151 (1993) 2296-2308); framework regions derived from the consensus sequence of human antibodies of a particular subgroup of light or heavy chain variable regions (see, e.g., Carter, P., et al., Proc. Natl. Acad. Sci. USA 89 (1992) 4285-4289; and Presta, L. G., et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M., et al., J. Biol. Chem. 272 (1997) 10678-10684 and Rosok, M. J., et al., J. Biol. Chem. 271 (19969 22611-22618).

In certain embodiments, the antibody is a human antibody. Human antibodies can be produced using various techniques known in the art. Human antibodies are described generally in van Dijk, M. A. and van de Winkel, J. G., Curr. Opin. Pharmacol. 5 (2001) 368-374 and Lonberg, N., Curr. Opin. Immunol. 20 (2008) 450-459.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, N., Nat. Biotech. 23 (2005) 1117-1125 and also, e.g., U.S. Pat. Nos. 6,075,181 and 6,150,584 describing XENOMOUSE™ technology; U.S. Pat. No. 5,770,429 describing HuMab® technology; U.S. Pat. No. 7,041,870 describing K-M MOUSE® technology, and US 2007/0061900, describing VelociMouse™ technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described (see, e.g., Kozbor, D., J. Immunol. 133 (1984) 3001-3005; Brodeur, B. R., et al., Monoclonal Antibody Production Techniques and Applications, Marcel Dekker, Inc., New York (1987), pp. 51-63; and Boerner, P., et al., J. Immunol. 147 (1991) 86-95). Human antibodies generated via human B-cell hybridoma technology are also described in Li, J., et al., Proc. Natl. Acad. Sci. USA 103 (2006) 3557-3562. Additional methods include those described, for example, in U.S. Pat. No. 7,189,826 (describing production of monoclonal human IgM antibodies from hybridoma cell lines) and Ni, J., Xiandai Mianyixue 26 (2006) 265-268 (describing human-human hybridomas). Human hybridoma technology (Trioma technology) is also described in Vollmers, H. P. and Brandlein, S., Histology and Histopathology 20 (2005) 927-937 and Vollmers, H. P. and Brandlein, S., Methods and Findings in Experimental and Clinical Pharmacology 27 (2005) 185-191.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Antibodies may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom, H. R., et al., Methods in Molecular Biology 178 (2001) 1-37 and further described, e.g., in the McCafferty, J., et al., Nature 348 (1990) 552-554; Clackson, T., et al., Nature 352 (1991) 624-628; Marks, J. D., et al., J. Mol. Biol. 222 (1992) 581-597; Marks, J. D. and Bradbury, A., Methods in Molecular Biology 248 (2003) 161-175; Sidhu, S. S., et al., J. Mol. Biol. 338 (2004) 299-310; Lee, C. V., et al., J. Mol. Biol. 340 (2004) 1073-1093; Fellouse, F. A., Proc. Natl. Acad. Sci. USA 101 (2004) 12467-12472; and Lee, C. V., et al., J. Immunol. Methods 284 (2004) 119-132.

In certain phage display methods, repertoires of VH and VL genes are separately cloned by polymerase chain reaction (PCR) and recombined randomly in phage libraries, which can then be screened for antigen-binding phage as described in Winter, G., et al., Ann. Rev. Immunol. 12 (1994) 433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths, A. D., et al., EMBO J. 12 (1993) 725-734. Finally, naive libraries can also be made synthetically by cloning non-rearranged V-gene segments from stem cells, and using PCR primers containing random sequence to encode the highly variable CDR3 regions and to accomplish rearrangement in vitro, as described by Hoogenboom, H. R. and Winter, G., J. Mol. Biol. 227 (1992) 381-388. Patent publications describing human antibody phage libraries include, for example, U.S. Pat. No. 5,750,373, and US 2005/0079574, US 2005/0119455, US 2005/0266000, US 2007/0117126, US 2007/0160598, US 2007/0237764, US 2007/0292936, and US 2009/0002360.

Antibodies or antibody fragments isolated from human antibody libraries are considered human antibodies or human antibody fragments herein.

In certain embodiments, the antibody is a multispecific antibody, e.g. a bispecific antibody. Multispecific antibodies are monoclonal antibodies that have binding specificities for at least two different sites. In certain embodiments, one of the binding specificities is for a first antigen and the other is for a different second antigen. In certain embodiments, bispecific antibodies may bind to two different epitopes of the same antigen. Bispecific antibodies may also be used to localize cytotoxic agents to cells which express the antigen. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A., et al., EMBO J. 10 (1991) 3655-3659), and "knob-inhole" engineering (see, e.g., U.S. Pat. No. 5,731,168). Multi-specific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M., et al., Science 229 (1985) 81-83); using leucine zippers to produce bi-specific antibodies (see, e.g., Kostelny, S. A., et al., J. Immunol. 148 (1992) 1547-1553; using "diabody" technology for making bispecific antibody fragments (see, e.g., Holliger, P., et al., Proc. Natl. Acad. Sci. USA 90 (1993) 6444-6448); and using single-chain Fv (sFv) dimers (see, e.g., Gruber, M., et al., J. Immunol. 152 (1994) 5368-5374); and preparing trispecific antibodies as described, e.g., in Tutt, A., et al., J. Immunol. 147 (1991) 60-69).

Engineered antibodies with three or more functional antigen binding sites, including "Octopus antibodies", are also included herein (see, e.g. US 2006/0025576).

The antibody can be a "Dual Acting Fab" or "DAF" comprising an antigen binding site that binds to a first antigen as well as another, different antigen (see, US 2008/0069820, for example).

The antibody or fragment can also be a multispecific antibody as described in WO 2009/080251, WO 2009/080252, WO 2009/080253, WO 2009/080254, WO 2010/112193, WO 2010/115589, WO 2010/136172, WO 2010/145792, or WO 2010/145793.

Methods

In certain embodiments, the methods provided herein are used to alter, i.e. to increase or decrease, the extent to which the antibody is glycosylated.

Where the antibody comprises an Fc-region, the carbohydrate attached thereto may be altered. Native antibodies produced by mammalian cells typically comprise a branched, biantennary oligosaccharide that is generally attached by an N-linkage to Asn297 of the CH2 domain of the Fc-region (see, e.g., Wright, A. and Morrison, S. L., TIBTECH 15 (1997) 26-32). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, the method provided results in the production of antibodies having a carbohydrate structure that lacks fucose attached (directly or indirectly) to an Fc-region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc-region (EU numbering according to Kabat of Fc-region residues); however, Asn297 may also be located about ±3 amino acids upstream or downstream of position 297, i.e., between positions 294 and 300, due to minor sequence variations in antibodies. Such fucosylation variants may have improved ADCC function (see, e.g., US 2003/0157108; US 2004/0093621). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki, A., et al., J. Mol. Biol. 336 (2004) 1239-1249; Yamane-Ohnuki, N., et al., Biotech. Bioeng. 87 (2004) 614-622. Examples of cell lines capable of producing defucosylated antibodies include Lec13 CHO cells deficient in protein fucosylation (Ripka, J., et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N., et al., Biotech. Bioeng. 87 (2004) 614-622; Kanda, Y., et al., Biotechnol. Bioeng. 94 (2006) 680-688; and WO 2003/085107).

In certain embodiments, the methods provided can be used to produce antibodies with bisected oligosaccharides, e.g., in which a biantennary oligosaccharide attached to the Fc-region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc-region can also be produced. Such antibody variants may have improved CDC function. Such antibody variants are described, e.g., in WO 1997/30087; WO 1998/58964; and WO 1999/22764.

Antibodies may be produced using recombinant methods and compositions, e.g., as described in U.S. Pat. No. 4,816,567. Nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp2/0). In one embodiment, a method of making an antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc-region effector function are not needed. For expression of antibody fragments and polypeptides in bacteria, see, e.g., U.S. Pat. Nos. 5,648,237, 5,789,199, and 5,840,523; see also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*. After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern (see Gerngross, T. U., Nat. Biotech. 22 (2004) 1409-1414; and Li, H., et al., Nat. Biotech. 24 (2006) 210-215).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts (see, e.g., U.S. Pat. Nos. 5,959,177, 6,040,498, 6,420,548, 7,125,978, and 6,417,429 (describing PLANTIBODIES™ technology for producing antibodies in transgenic plants)).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L., et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P., et al., Annals N.Y. Acad. Sci. 383 (1982) 44-68; MRC 5 cells; and FS4 cells. Other useful mammalian host cell lines include Chinese hamster ovary (CHO) cells, including DHFR negative (DHFR−) CHO cells (Urlaub, G., et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

II. Specific Aspects of the Invention

It has been found that depending on the vector organization the performance of the expression vector differs depending on the vector design in stable transfections.

It has been found without being bound by this theory that to the performance of the vector organization for stable transfections several points might contribute: 1) transcriptional interference phenomena between integrated vector copies in the host genome which depend on and are specific for the respective vector design and that do not exist in the transient system, 2) the influence of the selection process and selection stringency which depends on the respective vector organization and that plays an important role in the stable system, and 3) the optimal LC to HC polypeptide ratio.

It has been found that for stable transfections, however, the bidirectional expression of LC and HC was worse than the in row organization HC-LC-SM. Without being bound by this theory 1) the convergent organization of the expression cassettes for LC, HC and SM might reduce transcriptional interference phenomena between integrated vector copies, 2) the HC upstream of the LC obviously facilitates a LC to HC polypeptide ratio that is (more) optimal for stable transfections, and 3) the downstream position of the selection marker obviously increases stringency of selection. Moreover, the percentage of IgG producing cells and productivity of cell lines has been found to be increased. Increasing the concentration of selection pressure for vectors containing the selection marker bidirectionally upstream of the antibody expression cassettes did not increase productivity of stable pools or clones although stringency of selection clearly increased (data not shown).

It has been found that the hEF1α promoter generates a high number of well-producing and a very low number of non- or low-producing clones. However, product titers for the best individual clones of the hEF1α promoter in fed-batch analysis were lower than for clones of the hCMV promoter. But the overall number of top clones for the hCMV promoter is relatively low and their identification usually requires high screening efforts.

It has been found that the use of hGT significantly increased productivity for vectors containing the hCMV promoter when combined with the SV40 or bGH polyA signal in stable transfections. For vectors containing the hEf1α promoter, however, its effect on product titer was negligible when combined with the bGH polyA signal. Thus, it has been found that the influence of the hGT on the vector performance is dependent on the used promoter.

The choice of appropriate clones for the final evaluation in fully controlled large scale fermentations is usually based on batch or fed batch analysis in shake flasks. It has been found that differences in the performance and ranking of some expression vectors or elements between batch and fed-batch analysis are present. Replacing the SV40 by the bGH polyA signal increased productivity for vectors containing the hCMV promoter in batch but not in fed-batch analysis. The hGT has no significant influence on product titer of clones in batch but in fed-batch analysis. Absolute differences in the performance of vectors between batch and fed-batch partially differed. Differences between vectors differing in the position of selection marker or in the promoter (hEf1α or hCMV promoter) were moderately pronounced in batch—but strongly evident in fed-batch analysis. Expression levels and specific production rates—are higher in a fed-batch than in a batch mode.

A good correlation in the performance of fed-batch analysis and 2 L fermentations for most clones has been found, not only on level of absolute product titers, but also in ranking between different vectors and clones.

It has been found that the downstream position of the selection marker slightly reduced loss in productivity compared to the bidirectional position of the selection marker upstream of the antibody expression cassettes. Without being bound by theory, this might be due to an increased selection stringency and thus a higher mRNA level or by an improved LC to HC mRNA or polypeptide ratio. Both factors might lead to a higher tolerance towards changes in productivity.

The bGH polyA signal significantly decreased stability of antibody expression in clones compared to the SV40 polyA signal. However, the insertion of the hGT downstream of the bGH polyA signal clearly increased stability of expression. The positive effect of the hGT on stability was most apparent in absence of selection pressure. Stability analysis of stable pools revealed that cells rapidly lost productivity when generated with the hCMV but not when generated with the hEf1α promoter. Strikingly, although the hGT decreased productivity of clones for vectors containing the hEf1α promoter it slightly increased their stability.

Only a small portion of the clones significantly produced antibody after selection process. However, vector modifications in organization and/or elements significantly increased the ratio of IgG producing to non-producing clones. Different vector organizations and thus different expression levels of the selection marker that determine stringency of selection also clearly affect the percentage of IgG producing cells. Statistical simulations based on data of the screening process demonstrated that some expression vectors also bear the potential to decrease workload during screening process considerably. This fact has a major impact on costs for biopharmaceutical companies.

Expression Cassette Organization

Four different vectors with varying positions of the light and the heavy chain of the antibody and/or the selection marker were tested for their productivity (for details see FIG. 1).

Vectors p5137, p5156, p5158 and p5159 were tested in transient transfections and in batch analysis of stable pools. Vectors p5137 and p5156 were also tested in batch analysis of stable single clones.

Figure 2:
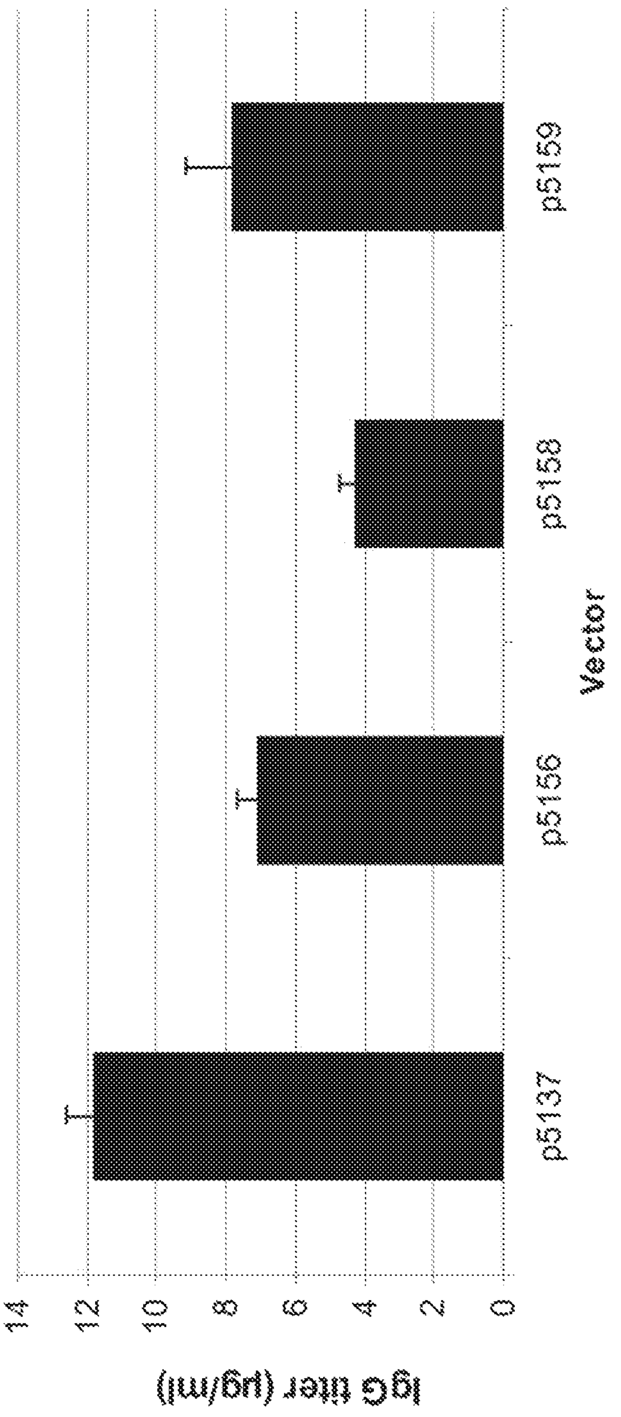

Vectors p5137, p5156, p5158 and p5159 were transiently transfected in CHO-K1 cells and productivity was determined by ELISA on day 5 after transfection (FIG. 2).

It has been found that for transient transfection the position of the heavy chain in front of the light chain of the antibody provides for better expression results compared to the inverse order. Thus, a higher productivity can be obtained: vector p5137—11.6 μg/ml; vector p5156—7.1 μg/ml; vector p5159—8.0 μg/ml; vector p5158—4.2 μg/ml.

It has been found that the position of the selection marker after both antibody chains provides for better expression results compared to the bidirectional position in front of the first antibody chain. Thus, a higher productivity can be obtained.

Vectors p5137, p5156, p5158 and p5159 were transfected in CHO-K1 cells by nucleofection and stable pools were selected. Productivity of the stable pools was determined in batch analysis.

Figure 3:
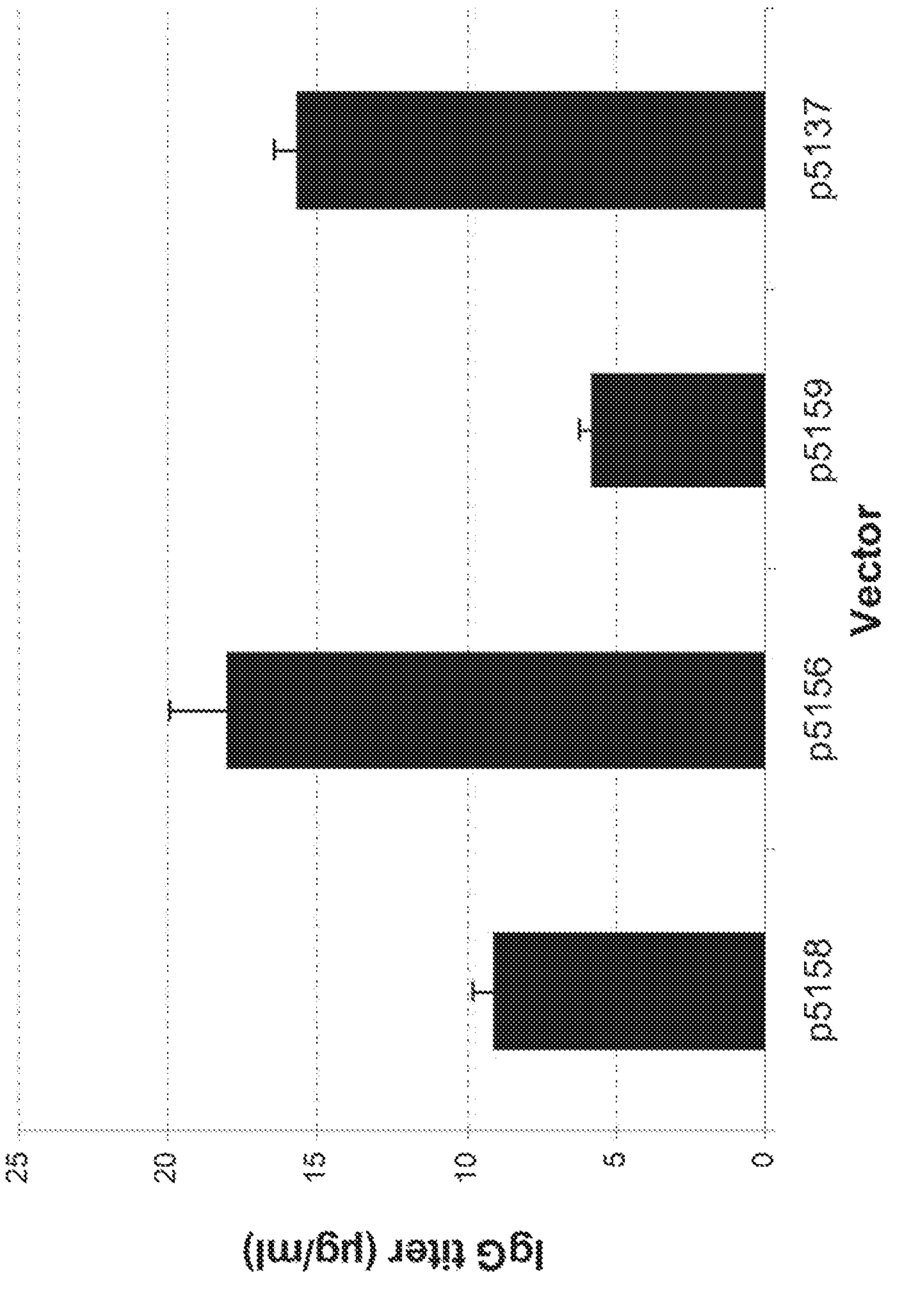

It has been found that the position of the selection marker after both antibody chains (in 5'-3' direction) provides for better expression results compared to the bidirectional position (3'-5' direction) in front of the first antibody chain. Thus, a higher productivity can be obtained: vector p5156—18.0 μg/ml; vector p5158—9.1 μg/ml; vector p5137—15.6 μg/ml; vector p5159—5.7 μg/ml (FIG. 3).

Vectors p5137 and p5156 were transfected into CHO-K1 cells by nucleofection. Stable transfected cells were selected and productivity of the best 15 clones was analyzed in batch analysis.

The average productivity of the best 15 clones generated with the vector p5137 and the vector p5156, respectively, were 159 μg/ml for the vector p5137 and 141 μg/ml for the vector p5156. The productivity distribution of the best 15 clones each vector in batch analysis is very similar. The productivities of the clones in batch analysis vary from about 50 μg/ml up to 300 μg/ml (one exception: the best clone generated with the vector p5137 reaches a productivity of >450 μg/ml).

The position of the selection marker after both antibody chains (in 5'-3' direction) leads to significantly higher productivities than the bidirectional 3'-5' position of the selection marker in front of the first antibody chain both in transient transfections and in batch analysis of stable pools.

It has been found that the position of the heavy antibody chain in front of the light antibody chain (both in 5'-3' direction) provides for better expression compared to the inverse order in transient transfections.

It has been found that the position/order of the light and the heavy antibody chains has no significant influence on productivity of stable pools and single clones. It has to be ensured that a slight excess of the light chain has to be expressed. Thus, the sequence of the antibody chain expression cassettes is arranged that this requirement is met.

It has been found that the antibody chain expression cassette (in any order) in front of/followed by the selection marker expression cassette (all in 5'-3' direction) is especially suited.

If two genes are expressed directly one after another the second gene is generally expressed at a lower rate. The read through of the RNA polymerase through the second transcription unit negatively influences transcription initiation at the promoter of the second transcription unit.

Figure 4:
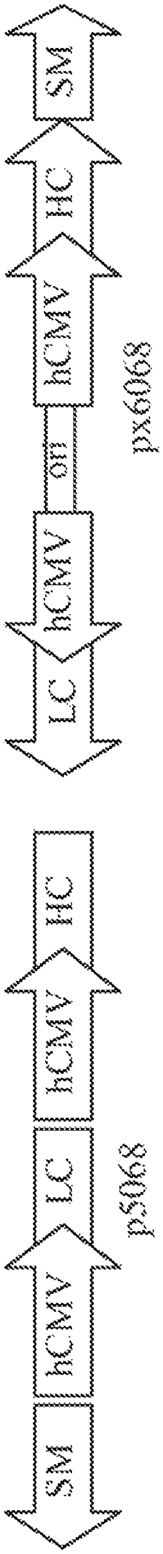

In vector px6068 the expression cassettes of the light and the heavy chain of the antibody were arranged bidirectional (FIG. 4).

To prevent promoter competition or interference (inefficient transcription initiation due to close proximity of two promoters, i.e. steric hindrance of promoter accession for transcription factors and the RNA polymerase, reduced availability of resources of the transcription machinery) the two short hCMV promoters driving the expression of the light and the heavy antibody chain were regionally separated (by the puc origin of replication).

Vectors p5068 and px6068 were transiently transfected in CHO-K1 cells by nucleofection.

Figure 5:
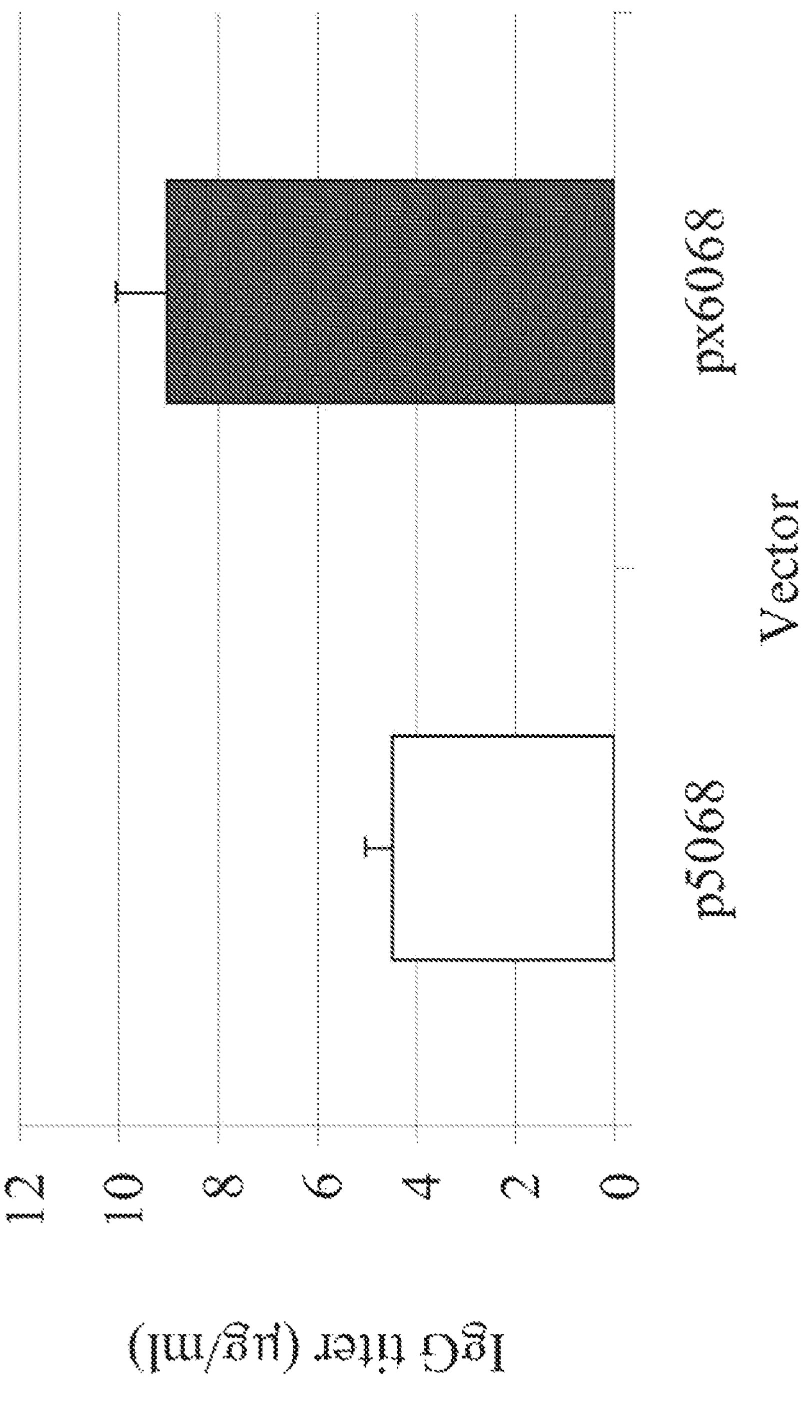

Vector px6068 showed an increased productivity in transient transfections compared to the expression vector p5068: 9.0 μg/ml for vector px6068, 4.5 μg/ml for vector p5068 (FIG. 5).

It has been found that the bidirectional and separated position of the light and the heavy chain of the antibody provides for an improved antibody expression compared to the back to back position of the light and the heavy chain in transient transfection.

Vectors p5068 and px6068 were transfected into CHO-K1 cells by nucleofection and stable pools were selected. Productivity of the stable pools was determined in batch analysis.

Batch analysis of stable pools showed that the productivity of the vectors p5068 and px6068 in stable pools is similar: 12.5 μg/ml for vector p5068; 12.5 μg/ml for vector px6068.

Transfection Protocol

For stable transfections vectors are linearized by restriction digestion with enzymes cutting in the backbone of the expression vector. In the case of the vector px6068 two possible restriction sites were possible:

1. between the transcription units of the light chain and the selection marker (SgrAI);
2. in the puc origin between the hCMV promoters of the light and the heavy chain (BssHII).

Vector px6068 linearized either by restriction digestion with SgrAI or BssHII was transfected into CHO-K1 cells by nucleofection and stable pools were selected. Productivity of the stable pools was determined in batch analysis.

It has been found that the position of the linearization site in the expression vector apparently has an influence on productivity of the vectors in batch analysis of stable pools.

Pools generated with the vector px6068 linearized by the restriction enzyme BssHII show higher productivities compared to stable pools generated with the vector px6068 linearized by the restriction enzyme SgrAI: $1^{st}$ experiment: 6.4 µg/ml for vector px6068 linearized by the restriction enzyme BssHII and 2.8 µg/ml for vector px6068 linearized by the restriction enzyme SgrAI; $2^{nd}$ experiment: 12.5 µg/ml for vector px6068 linearized by the restriction enzyme BssHII and 9.6 µg/ml for vector px6068 linearized by the restriction enzyme SgrAI (see FIG. 6).

Time Point of Start of Selection Pressure

The selection pressure was exerted at different time points after transfection, i.e. at 0 hours, 4 hours, 8 hours, 24 hours, and 48 hours, for the generation of stable cell clones.

Figure 7:
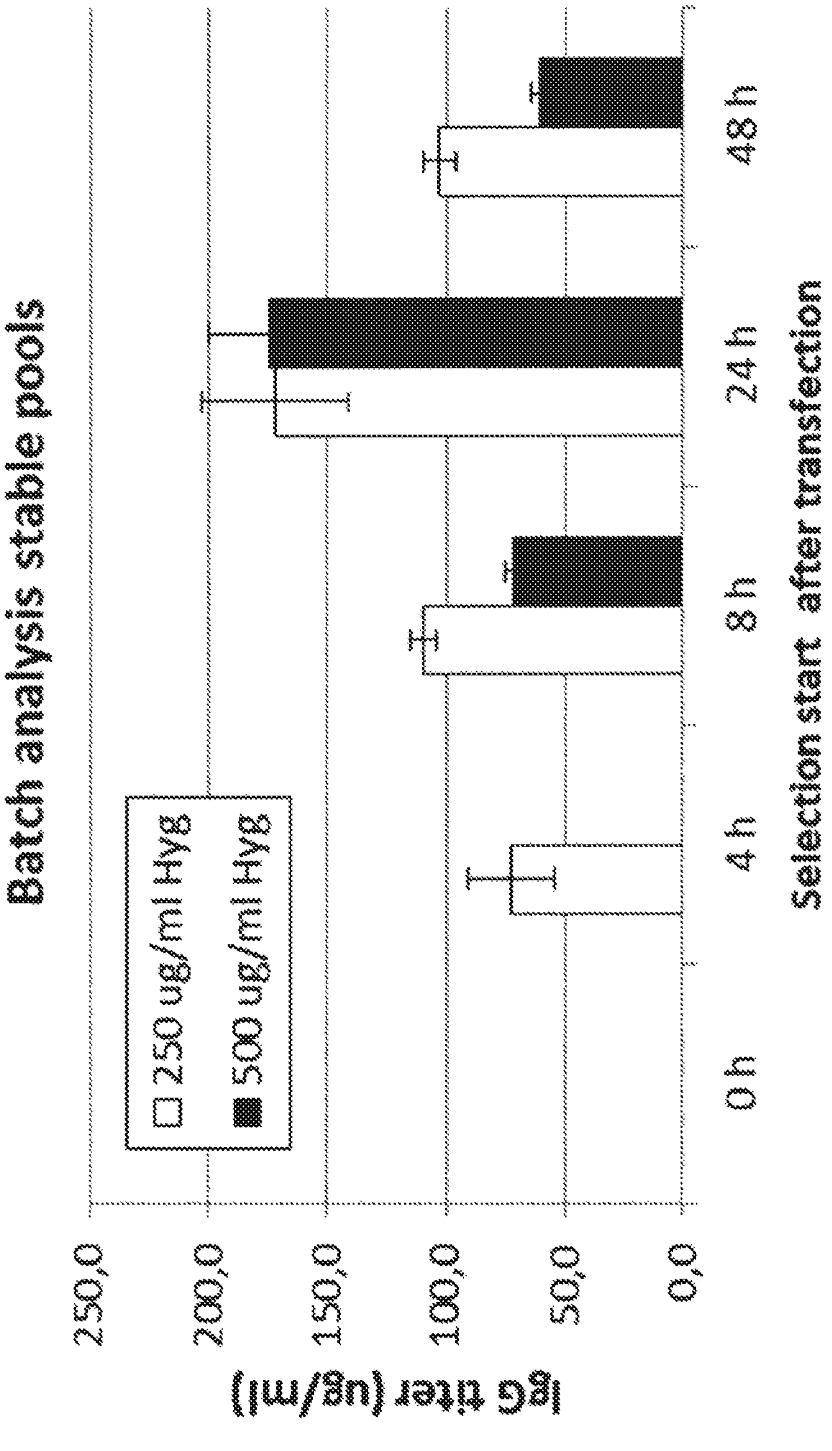

It has been found that by the addition of the selection pressure 24 hours after transfection independently of the concentration of the selection agent results in the highest antibody titer in the cultivation supernatant (see FIG. 7).

Influence of Vector Backbone on Performance of Cell Lines

Generally an expression vector is linearized prior to the transfection into a eukaryotic cell. Additionally expression vectors comprise prokaryotic sequences required for the amplification of the expression vector in prokaryotic cells.

It has been found that the removal of the prokaryotic elements from the linearized expression vector prior to the transfection into eukaryotic cells results in

- reduction of the required selection time for the generation of stable cell clones (FIG. 8*a*),
- enhanced productivity of pools (FIG. 8*b*) and single clones (FIG. 8*c*),
- accelerated recovery (FIG. 8*d*), and
- improved cell growth (FIG. 8*e*).

Vector Elements and Expression Cassette Orientation

Several different transcriptional relevant genetic elements and combinations thereof have been compared to a reference genetic element combination. On the basis of comparative transient experiments the following results have been obtained (see table below, bidirectional vector organization, SM (3"-5")-LC_HC (5'-3'))).

| genetic element in vector px5068 | inserted element | result in transient experiments | results in stable experiments |
|---|---|---|---|
| no transcription terminator | | | |
| | hGT transcription terminator | enhanced expression (+31%) | enhanced expression: +37%, stable pools; +23% single clones |
| SV40 polyA signal | replaced by element | | |
| | bGH polyA signal | enhanced expression (+46%) | stable pools: +38%; single clones: −8% (for 15 best clones) |
| | bGH polyA + hGT | enhanced expression (+58%) | enhanced expression: stable pools +63%; single clones +40% (for 15 best clones) |

-continued

| genetic element in vector px5068 | inserted element | result in transient experiments | results in stable experiments |
|---|---|---|---|
| short hCMV promoter | | | |
| | full length hCMV + Intron A | enhanced expression (+134%) | pool: enhanced expression (+23%) single clones: reduced expression (−62% for best 15 clones) |
| | rat hCMV + Intron A | reduced expression (−50%) | Stable pools, reduced expression (−40%) |
| | hEF1α + Intron A | increased expression (+53%) | pool:enhanced expression (+460%) clones: −16% for best 15 clones (batch) |

Different promoters have been combined with the bGH polyA signal and the hGT transcription terminator (see table below).

| genetic elements in vector px5068 | replaced by element | result in transient experiments | results in stable experiments |
|---|---|---|---|
| short hCMV promoter SV40 polyA signal | | | |
| | full length hCMV promoter with Intron A bGH polyA signal hGT transcription terminator | increased expression (+75%) | single clones: reduced expression (−34% for best 15 clones) |
| | hEf1α promoter with Intron A bGH polyA signal hGT transcription terminator | increased expression (+20%) | single clones: similar expression (−1%) |

Used Vectors:

| vector | promoter | polyA signal | transcription terminator |
|---|---|---|---|
| px5068 | short hCMV without Intron A | SV40 polyA signal | no transcription terminator |
| px6001 | short hCMV without Intron A | SV40 polyA signal | hGT transcription terminator |
| px6008 | short hCMV without Intron A | bGH polyA signal | no transcription terminator |
| px6007 | short hCMV without Intron A | bGH polyA signal | hGT transcription terminator |
| px6051 | full length hCMV with Intron A | SV40 polyA signal | no transcription terminator |
| px6052 | hEF1α promoter with Intron A | SV40 polyA signal | no transcription terminator |
| px6053 | rat CMV promoter with Intron A | SV40 polyA signal | no transcription terminator |
| px6062 | full length hCMV with Intron A | bGH polyA signal | hGT transcription terminator |
| px6063 | hEF1α promoter with Intron A | bGH polyA signal | hGT transcription terminator |

It has been found that an increased expression (productivity) using the vector elements/element combination as reported herein can be achieved:

human CMV without Intron A: 100% (reference)
human CMV with Intron A: transient 234%, pool 123%, clones 38%
rat CMV with Intron A: transient 50%, pool 60%
human EF1α with Intron A: transient 153%, pool 564%, single clones: 84% (SV40 polyA) approx. 100% (bGH and hGT)
human EF1α with Intron A and: +40% (to human EF1a) optimized 5'UTR
MPSV: 29%
bGH polyA: transient 146%, pool+38%, stable clones 92%
hGT: transient 131%, stable pools 137%, single clones 123%
bGH polyA and hGT: transient 158%, stable pools 163%, single clones 140% human CMV promoter:
Xu et al., J. Control. Release, 81 (2002) 155-163.
Xia et al., Prot. Expr. Purif. 45 (2006) 115-124.
rat CMV promoter:
Xia et al., Prot. Expr. Purif. 45 (2006) 115-124.
human EF1α promoter:
Teschendorf et al., Anticancer Res. 22 (2002) 3325-3330.
Li et al., J. Immunol. Methods 318 (2007) 113-124.
MPSV promoter:
Xia et al., Prot. Expr. Purif. 45 (2006) 115-124.
Artelt et al., Gene 68 (1988) 213-219.
Stocking et al., Proc. Natl. Acad. Sci. USA 82 (1985) 5746-5750.
Lin et al., Gene 147 (1994) 287-292.
MPSV-CMV hybrid promoter:
Liu et al., Anal. Biochem. 246 (1996) 150-152.

A high selectivity and high stringency selection process can be provided by using an IRES-linked expression cassette for the expression of the selection marker:

selection pressure on antibody expression results in high selectivity
linked expression of antibody and selection marker results in high selectivity
it has been found that use of an IRES element with weak activity results in high stringency, i.e. high antibody production and low selection marker production
linking the expression of antibody and selection marker by IRES elements
identification of IRES elements (EMCV/Gtx) with weak activity which do alter IgG expression marginally
use of a fusion protein working as selection and as screening marker
bifunctional GFP-Neomycin fusion protein
PEST sequence of the ornithine decarboxylase is a strong proteolytic signal sequence and confers a reduced half-life of the protein
IRES linked expression of the fusion protein results in high selectivity
short half-live by proteolytic signal sequence results in high stringency
due to weak expression and short half-life of the fusion protein a strong expression is required rapid identification of high producers by FACS (sorting of high GFP expressing clones provides for selection of high producers)

Selection marker linked to heavy antibody chain by different IRES elements

| | |
|---|---|
| px5068 (without IRES): | 100% antibody expression (reference) |
| Gtx-IRES: | 20-27% |
| EMCV-IRES | 81-94% |
| EV71-IRES | 20-36% |
| ELF4G-IRES | 3-17% |
| Gtx-IRES (synthetic) | 88% |

GFP-Neo Fusion protein linked to heavy antibody chain by different IRES elements

| | Gtx | EV71 | ELF4G | EMCV |
|---|---|---|---|---|
| GFP expression: | + | +++ | – | + |
| antibody expression: | – | – | – | + |

Gtx-IRES:
Komuro et al., EMBO J. 12 (1993) 1387-1401.
EMCV-IRES:
Mountford et al., Proc. Natl. Acad. Sci. USA 91 (1991) 4303-4307.
EV71-IRES:
Lee et al., Biotechnol. Bioeng. 90 (2005) 656-662.
ELF4G-IRES:
Wong et al., Gene Ther. 9 (2002) 337-344.
Gtx (synthetic)-IRES:
Chappell et al., Proc. Natl. Acad. Sci. USA 97 (2000) 1536-1541.

It has been found that an increased expression (productivity) using the linking of the light chain expression cassette to the heavy chain expression cassette can be achieved by the EV71-IRES element:

px5068 without IRES: 100% antibody expression (reference)
Gtx-IRES (synthetic): 3%
EV71-IRES: 82%
ELF4G-IRES: 5%
EMCV-IRES: 7%

Vector Elements in Combination with Vector Organization

The following vectors were tested in a CHO-K1 host cell line in transient transfections, in stable pools and on single clone level.

| vector | organization | promoter | polyA signal | transcription terminator |
|---|---|---|---|---|
| px9001 | SM(3'-5')-LC-HC | hCMV | SV40 polyA | not present |
| px9002 | LC-HC-SM | hCMV | SV40 polyA | not present |
| px9003 | LC-HC-SM | hEF1α | SV40 polyA | not present |
| px9004 | LC-HC-SM | hCMV | bGH polyA | not present |
| px9005 | LC-HC-SM | hCMV | bGH polyA | hGT |
| px9006 | LC-HC-SM | hEF1α | bGH polyA | not present |
| px9007 | LC-HC-SM | hEF1α | bGH polyA | hGT |
| px9010 | LC(3'-5')-HC-SM | hEF1α | bGH polyA | not present |
| px9011 | LC(3'-5')-HC-SM | hCMV | SV40 polyA | hGT |

Several transcription related genetic elements and combinations thereof have been compared to a reference vector (px9001, vector organization SM (3'5' orientation)-LC-HC (5'-3' orientation)). On the basis of comparative experiments the following results have been obtained for the unidirectional vector organization with the expression cassette for the light and heavy chain (light chain expression cassette upstream of the heavy chain expression cassette) and for the selection marker in same direction (see table below) compared to a reference vector (px9001, bidirectional vector organization SM (3'5')-LC-HC (5'-3')).

| Reference vector px9001 (bidirectional, SM (3'-5')-LC_HC (5'-3')) or px9002 (unidirectional, LC-HC-SM (5'-3')) | inserted element | result in transient experiments | results in stable experiments |
|---|---|---|---|
| | no differing elements but different vector organization (px9002, LC-HC-SM) | reduced expression of px9002 compared to px9001 (−10%) | single clones +37% in batch and +80% in fed batch analysis for px9002 compared to px9001 |

| genetic element in vector px9002 (LC-HC-SM) | inserted element | result in transient experiments | results in stable experiments |
|---|---|---|---|
| SV40 polyA signal | replaced by element bGH polyA signal (px9004) | enhanced expression (+15% compared to px9002) | stable pools +115%; single clones +61% and +58% in batch and fed batch analysis for the best 36 and 15 clones, respectively (compared to px9001) |
| | bGH polyA + hGT (px9005) | enhanced expression (+30% compared to px9002) | stable pool +125%; single clones +53% and +92% in batch and fed batch analysis for the best 36 and 15 clones, respectively (compared to px9001) |

| Reference vector px9001 (bidirectional, SM (3'-5')-LC_HC (5'-3')) or px9002 (unidirectional, LC-HC-SM (5'-3')) | inserted element | result in transient experiments | results in stable experiments |
|---|---|---|---|
| short hCMV promoter + SV40 polyA | | | |
| | hEF1α + Intron A + SV40 polyA (px9003) | increased expression (+34% compared to px9002) | stable pool: enhanced expression, +596%; clones: single clones +53% and +92% in batch and fed batch analysis for the best 36 and 15 clones, respectively (compared to px9001) |
| | hEF1α + Intron A + bGH polyA (px9006) | increased expression (+50% compared to px9002) | stable pool: enhanced expression +704%; single clones +19% and −7% in batch and fed batch analysis for the best 36 and 15 clones, |

-continued

| | | |
|---|---|---|
| | | respectively (compared to px9001) |
| hEF1α + Intron A + bGH polyA + hGT (px9007) | increased expression (+47% compared to px9002) | pool: enhanced expression +583% clones: single clones +7% and −14% in batch and fed batch analysis for the best 36 and 15 clones, respectively (compared to px9001) |

Figure 9:
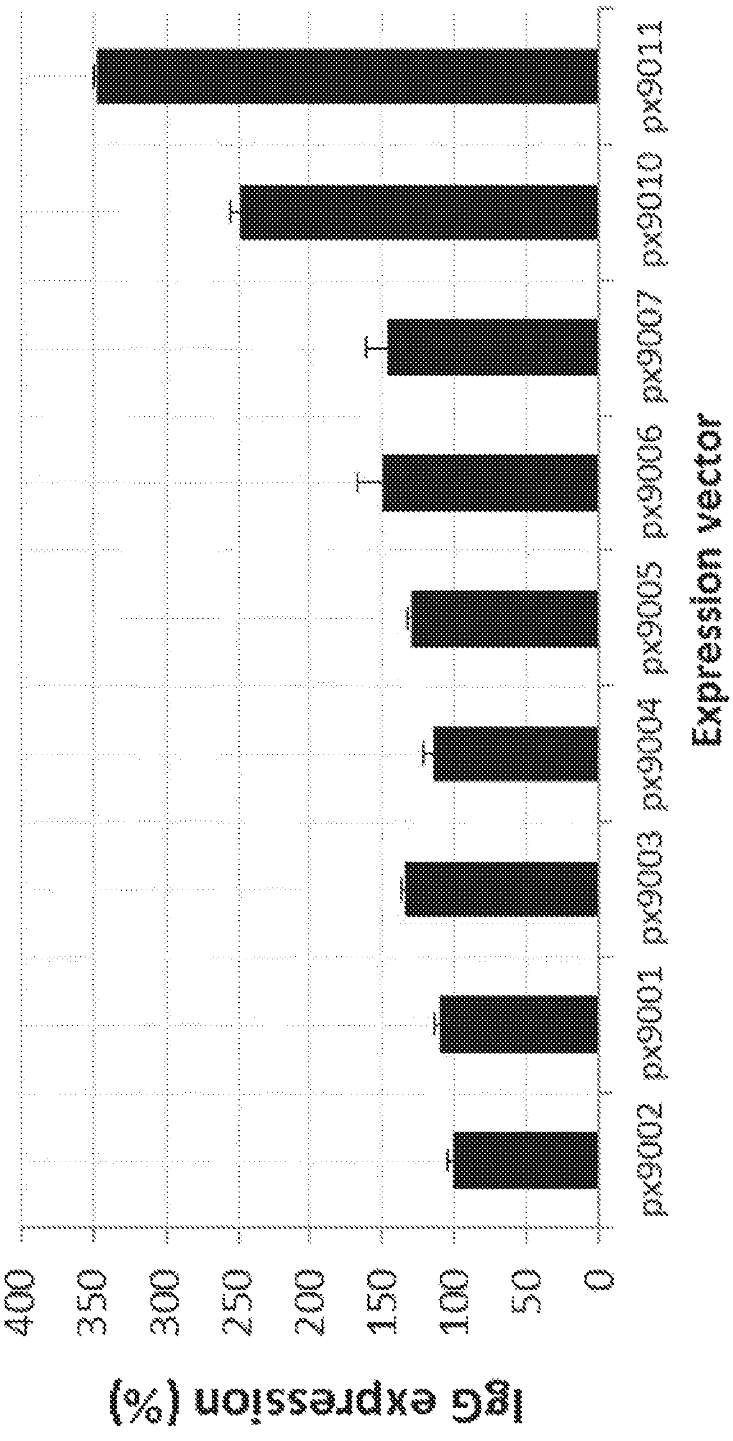

Performance of different vectors in transient transfections was tested after nucleofection into CHO-K1 cells (see FIG. 9).

Vectors containing the human elongation factor 1 alpha promoter (hEF1α) (based on the vector organization LC-HC-SM) have an increased productivity of about +34% (px9003 versus px9002; SV40 polyA signal sequence) and +30% (px9006 versus px9004; bGH polyA signal sequence), dependent on the used polyA signal sequence, respectively, compared to the use of the hCMV promoter.

The addition of the human gastrin terminator (hGT) to the bGH polyA signal sequence has a positive effect on productivity for vectors containing the hCMV-(px9005 versus px9004; +13%).

Expression vectors based on the bidirectional expression of the light and the heavy chain of the antibody show improved performance. Product titers are about 2.7 to 3.4 fold increased compared to the control vector px9001 dependent on the used promoter (hEF1α or hCMV) and the used polyA signal sequence (SV40 or bGH polyA signal sequence).

It has been found that the use of human elongation factor 1 alpha promoter and the bGH polyA signal sequence has a positive effect on productivity in the vector organization LC-HC-SM (+50%; compare px9006 and px9002) but not in vector organization LC(3'-5')-HC-SM (−28%; compare px9010 and px9011).

To compare the productivity of the expression vector px9002 with the vectors px9003-9007 vectors were transfected into CHO-K1 cells by nucleofection and stable pools were selected. Productivity of the pools was analyzed in batch analysis (see FIG. 10).

Batch analysis of stable pools showed that antibody titers from pools transfected with the vector containing the human elongation factor 1 alpha promoter (px9003, px9006, px9007) were approximately 7-8 fold higher than those of cells transfected with the reference vector containing the short-length hCMV promoter (vector px9002) (compare 97.5 μg/ml, 112.5 μg/ml and 95.6 μg/ml and for vectors px9003, px9006 and px9007 versus 14.0 μg/ml for vector px9002.

Vectors px9001, px9002 and px9004 to px9007 were transfected into CHO-K1 cells by nucleofection and best single clones were identified by classical screening process. Productivity of best 36 clones each vector were analyzed in batch analysis and best 15 clones in batch analysis were tested in fed batch analysis.

The average productivity of the best 36 single clones generated with the vector px9001 in batch analysis is 356 μg/ml. Clones generated with the vector px9002 or with the vectors px9004 and 9005 (additionally containing the BGH PolyA signal (alone or in combination with the HGT) instead the SV40 PolyA signal) show a 37% (px9002) respectively 61% (px9004) to 53% (px9005) increase in productivity compared to the control vector px9001. Clones of vector px9006 and px9007 show an increase in productivity of about 19% and 7% respectively.

In fed batch experiments best 15 clones obtained with each vector in batch analysis were tested in fed batch analysis over 14 days.

The average productivity of the best 15 in house single clones (generated with vector px9001) in fed batch analysis is 1345 μg/ml. Clones generated with the vector px9002 or with the vectors px9004 and px9005 (additionally containing the bGH polyA signal sequence (alone or in combination with the hGT) instead of the SV40 polyA signal sequence) show a 80% (px9002) respectively 58% (px9004) to 92% (px9005) increase in productivity compared to the control vector px9001.

Beside an increased average productivity (see above) also the performance of the top clones is strongly improved. Vectors px9002, px9004 and px9005 show—with regard to productivity of the top 5 clones an increase of about 64% (px9002), 50% (px9004) and 88% (px9005) compared to control vector px9001.

In the following the percentage of producing respectively non-producing cells for each of the different vectors was compared directly. 14.2% of clones generated with vector px9001 produce antibody, in the rest of the resistant clones antibody expression is either silenced or clones have other defects.

The vector organization of vector px9002 almost doubled the percentage of producing cells (to 26.0%). Vector additionally containing the bGH PolyA signal sequence alone instead the SV40 polyA signal sequence either alone (vector px9004) or in combination with the hGT (vector px9005) show an approximately 3 fold increase in percentage of producing cells (39% and 43%, respectively).

The use of the human elongation factor 1 alpha promoter instead of the hCMV promoter increased the number of producing cells up to 5 fold (more than 70% of the clones obtained after the selection process do really produce antibody).

The 15 best clones obtained by transfection with vectors px9001-9007 (based on fed batch results) were cultivated in the presence and in the absence of Hygromycin B for 15 passages (=approximately 60 generations). Product titers of clones in batch analysis after 15 passages were compared with product titer of clones in batch at the beginning of stability test.

In the presence of selection pressure the change in product titer between 15 clones of each vector varies from −14.7% for vector px9007 and +0.2% for vector px9002 after 15 passages.

In the absence of selection pressure the decrease in product titer varies from 25.5% for vector px9004 up to 5.9% for vector px9005.

The number of clones that fulfill defined stability criteria such as >80% of product titer in batch analysis compared to values at starting point (GO) both in the presence and in the absence of selection marker varies from 4-10. Vectors px9005, px9007 and px9002 lead to the highest number of stable clones likewise in the presence and absence of selective pressure/selection marker (px9005: 10; px9007: 7; px9002:6)).

Thus, it has been found that the organization of vectors px9005 shows positive effects on stability and increase number of stable clones, especially in the absence of selection pressure.

It has been found that the combination of the bGH polyA and the hGT compared to the SV40 polyA without transcription terminator (hGT) clearly increases productivity of stable clones independent of the used promoter.

Transient Transfections:
- the use of the human elongation factor 1 alpha promoter (with Intron A) provides for an enhanced productivity (in LC-HC-SM organization)
- the use of the bovine growth hormone polyA signal sequence provides for an enhanced productivity compared to use of the SV40 polyA signal sequence
- the addition of the HGT to the bGH PolyA signal sequence results in an increased productivity in vectors containing the hCMV promoter
- vector organization LC(3'-5')-HC-SM results in improved expression Stable Pools
- pools generated with vectors containing the hEF1α promoter show an enhanced productivity in batch analysis
- clones generated with vectors containing the hEF1α promoter show a reduced number of low producing clones
- clones generated with vectors containing the hEF1α promoter show a higher stability of IgG expression Single Clones
- vector organization with downstream position of selection marker (LC-HC-SM) has a positive effect on productivity of single clones
- clones generated with vectors containing the bGH polyA signal sequence and the hGT have higher productivities and stabilities The following examples, figures and sequences are provided to aid the understanding of the present invention, the true scope of which is set forth in the appended claims. It is understood that modifications can be made in the procedures set forth without departing from the spirit of the invention.

Sequences

SEQ ID NO: 01 short human CMV promoter without Intron A

SEQ ID NO: 02 short human CMV promoter without Intron A with 5'UTR

SEQ ID NO: 03 full length human CMV promoter with Intron A

SEQ ID NO: 04 full length human EF1 alpha promoter without Intron A

SEQ ID NO: 05 full length human EF1 alpha promoter with Intron A

SEQ ID NO: 06 short human EF1 alpha promoter with Intron A with 5'UTR

SEQ ID NO: 07 full length rat CMV promoter with Intron A

SEQ ID NO: 08 SV40 polyA signal sequence

SEQ ID NO: 09 bGH polyA signal sequence

SEQ ID NO: 10 hGT terminator sequence

SEQ ID NO: 11 SV40 promoter

SEQ ID NO: 12 PEST sequence of ornithine decarboxylase

SEQ ID NO: 13 nucleic acid sequence encoding GFP

SEQ ID NO: 14 neomycin selection marker

SEQ ID NO: 15 GFP-PEST-NEO fusion polypeptide encoding nucleic acid

SEQ ID NO: 16 EMCV-IRES

SEQ ID NO: 17 EV71-IRES

FIGURES

FIG. 1 Schematic overview on different vector designs tested in transient transfections, in stable pools and on single clone level. Vector p5158, p5137, p5156 and p5159 vary in the position of the light (LC) and the heavy chain (HC) respectively and/or in the position of the selection marker (SM).

FIG. 2 Productivity of vectors p5137, p5156, p5158 and p5159 in transiently transfected CHO-K1 cells. Shown is the average productivity of eight independent transfections each vector on day 5 after transfection measured by ELISA.

FIG. 3 Productivity of stable pools generated with the vectors p5137, p5156, p5158 and p5159 in batch analysis. Shown is the average productivity of three pools each vector on day 7.

FIG. 4 Schematic overview of the vector design of the expression vector p5068 and of the vector design of the vector px6068. LC (light chain), HC (heavy chain), SM (selection marker (driven by a SV40 promoter)) and ori (origin of replication) are indicated.

FIG. 5 Productivity of vectors p5068 and px6068 in transiently transfected CHO-K1 cells. Shown is the average productivity of eight independent transfections of each vector on day 7 after transfection measured by ELISA.

Figure 6:
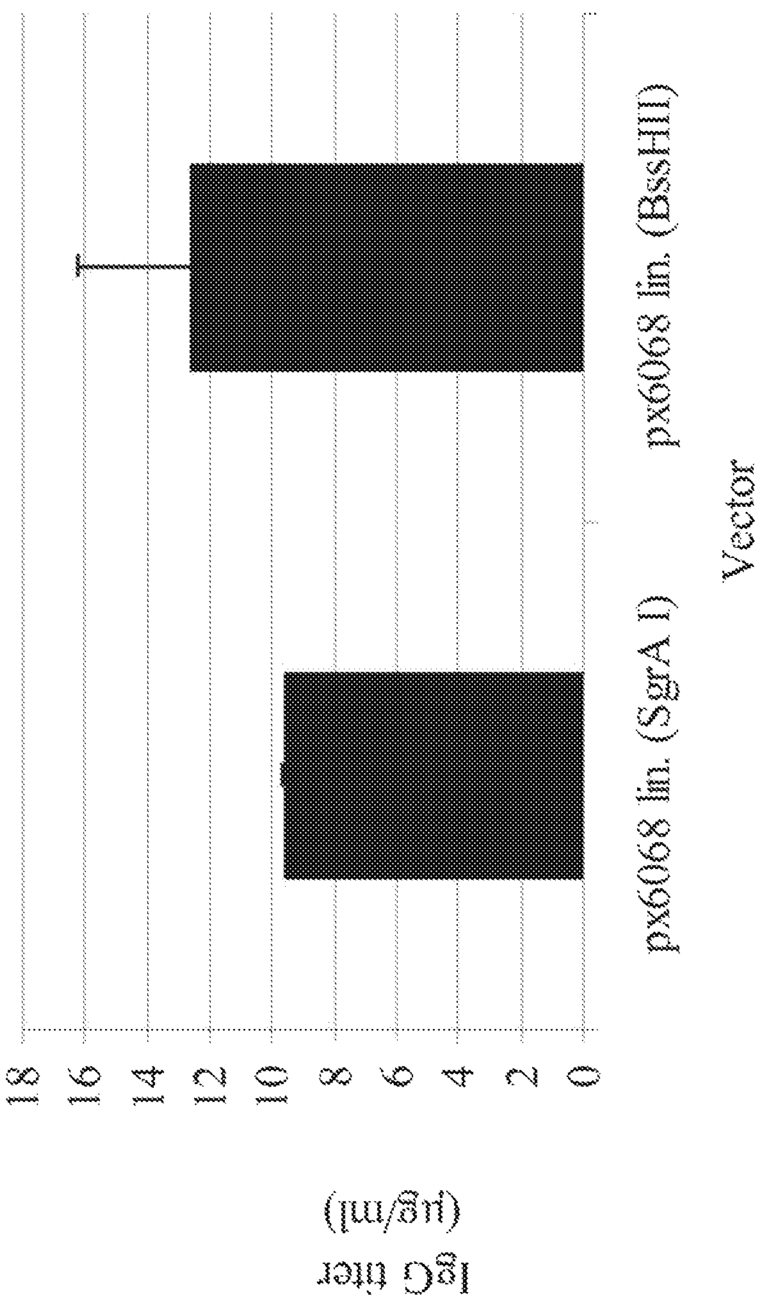

FIG. 6 Productivity of stable pools generated with the vector px6068 linearized either by the restriction enzyme SgrAI or by the restriction enzyme BssHII. Shown is the average productivity of two pools each vector in batch analysis on day 7.

FIG. 7 Dependence of the IgG titer of stable cell pools on the time point of the start of the selection after transfection.

Figure 8:
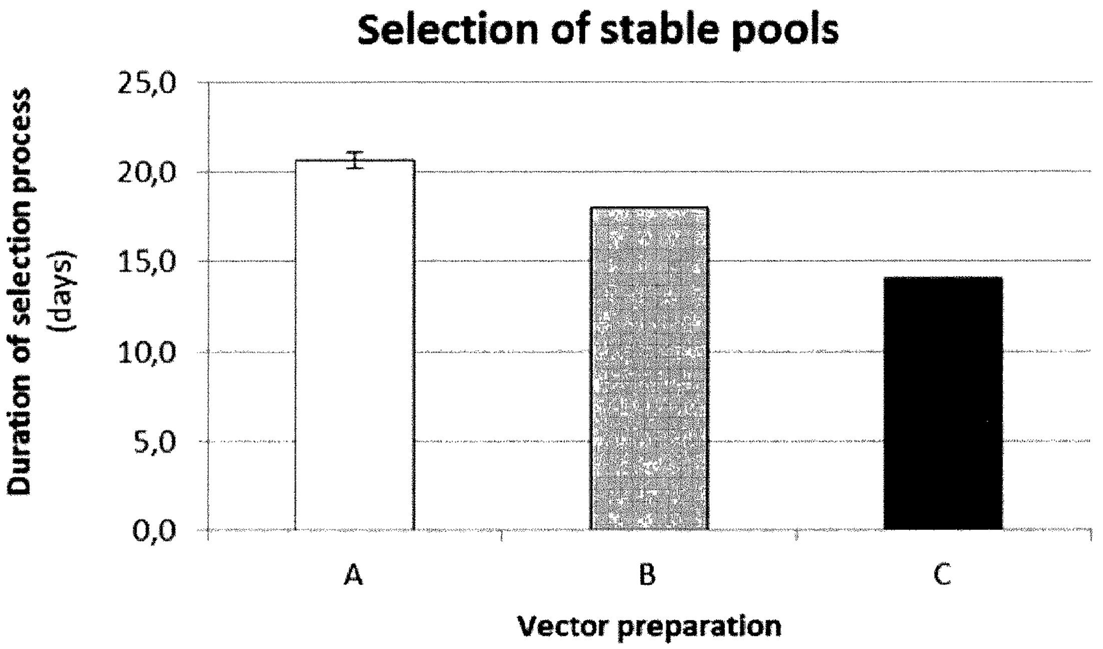
Figure 8:
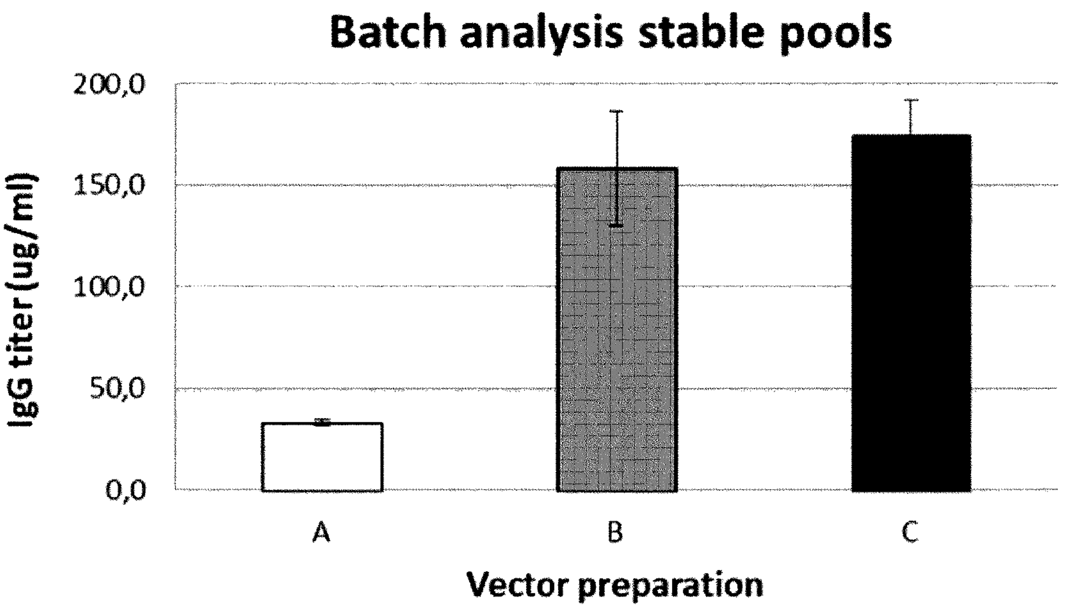
Figure 8:
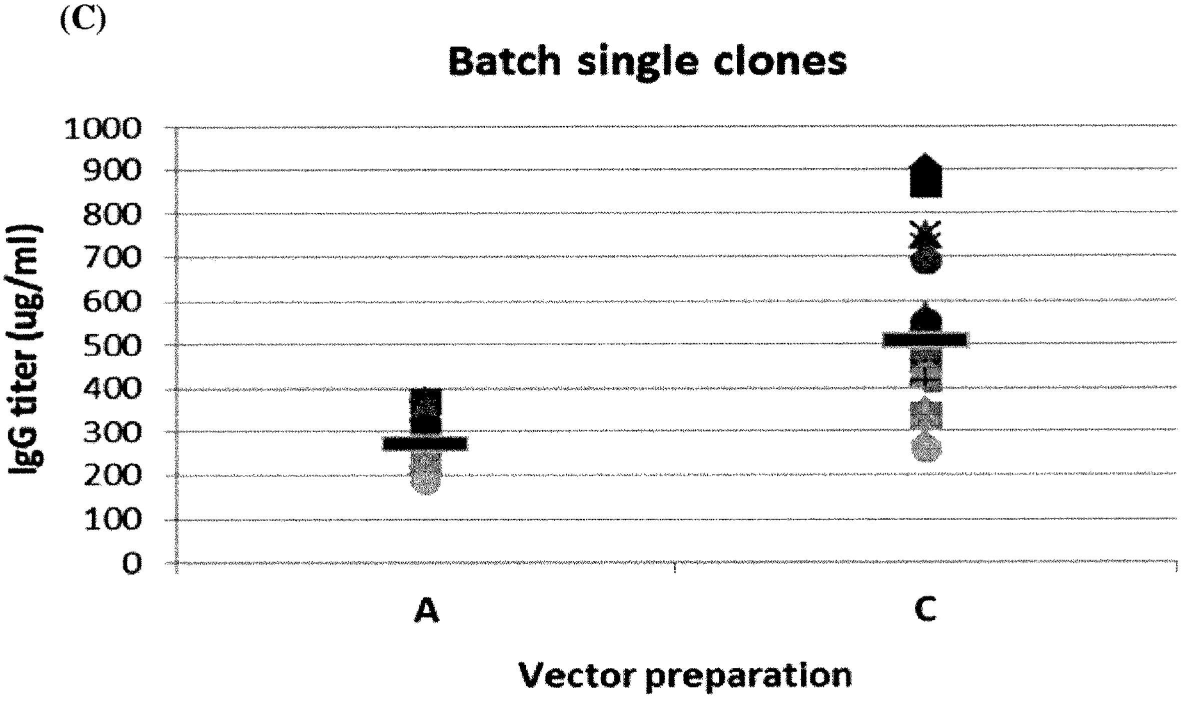
Figure 8:
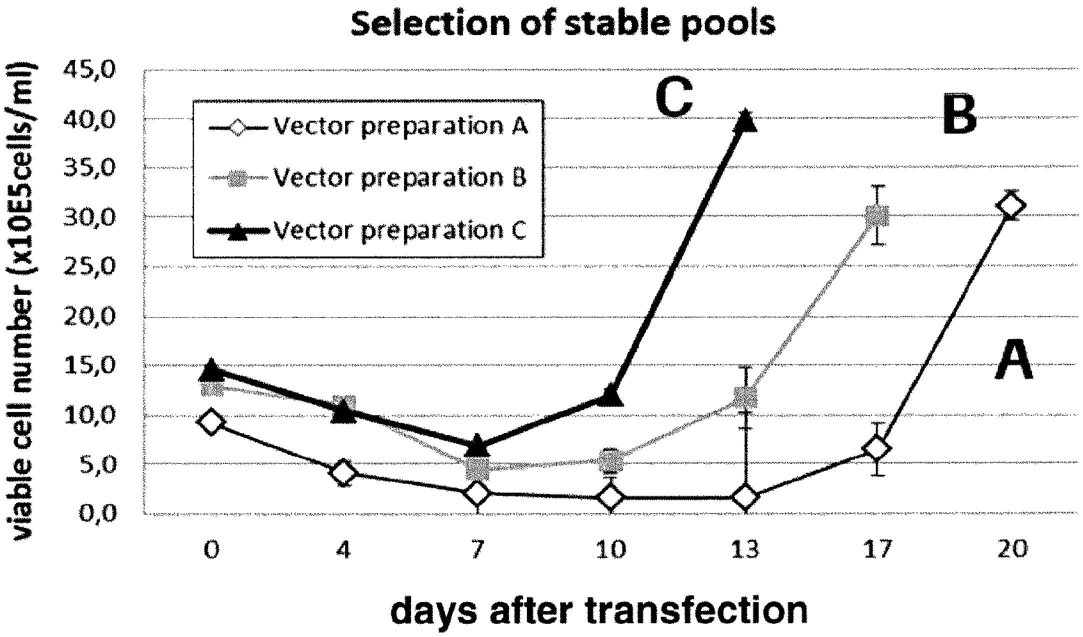
Figure 8:
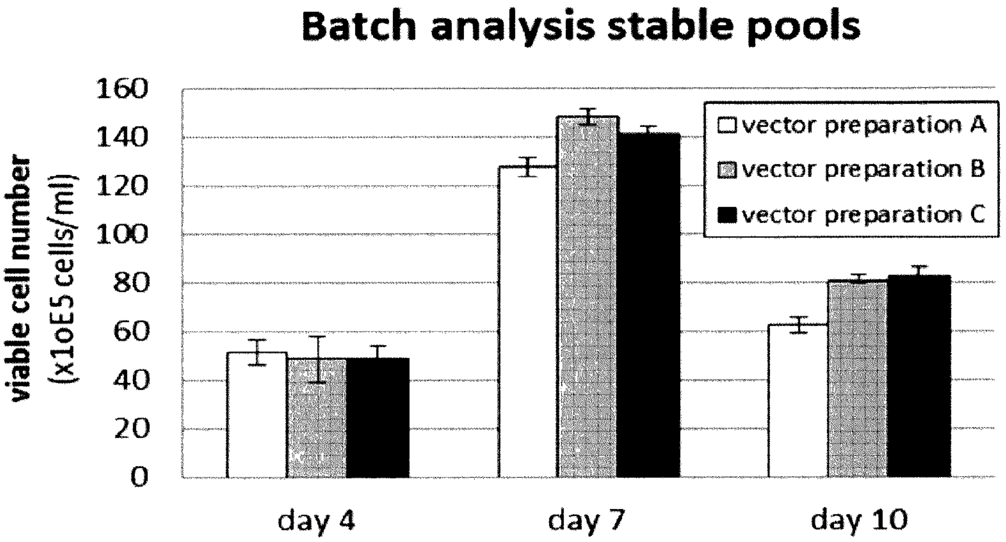

FIG. 8 (A) selection time for the generation of stable cell clones; (B) productivity of pools; (C) productivity of single clones; (D) time course of viable cell density recovery; (E) viable cell density after 4, 7 and 10 days of cultivation; vector preparation A—linearized entire vector, vector preparation B—cutting out of prokaryotic vector elements, vector preparation C—cutting out and removal of prokaryotic vector elements.

FIG. 9 Productivity of vectors px9001-px9011 in transient transfections using nucleofection: Shown is the average productivity of eight independent transfections of each vector on day six after transfection; values are normalized to values of reference px9001 (set to 100%).

Figure 10:
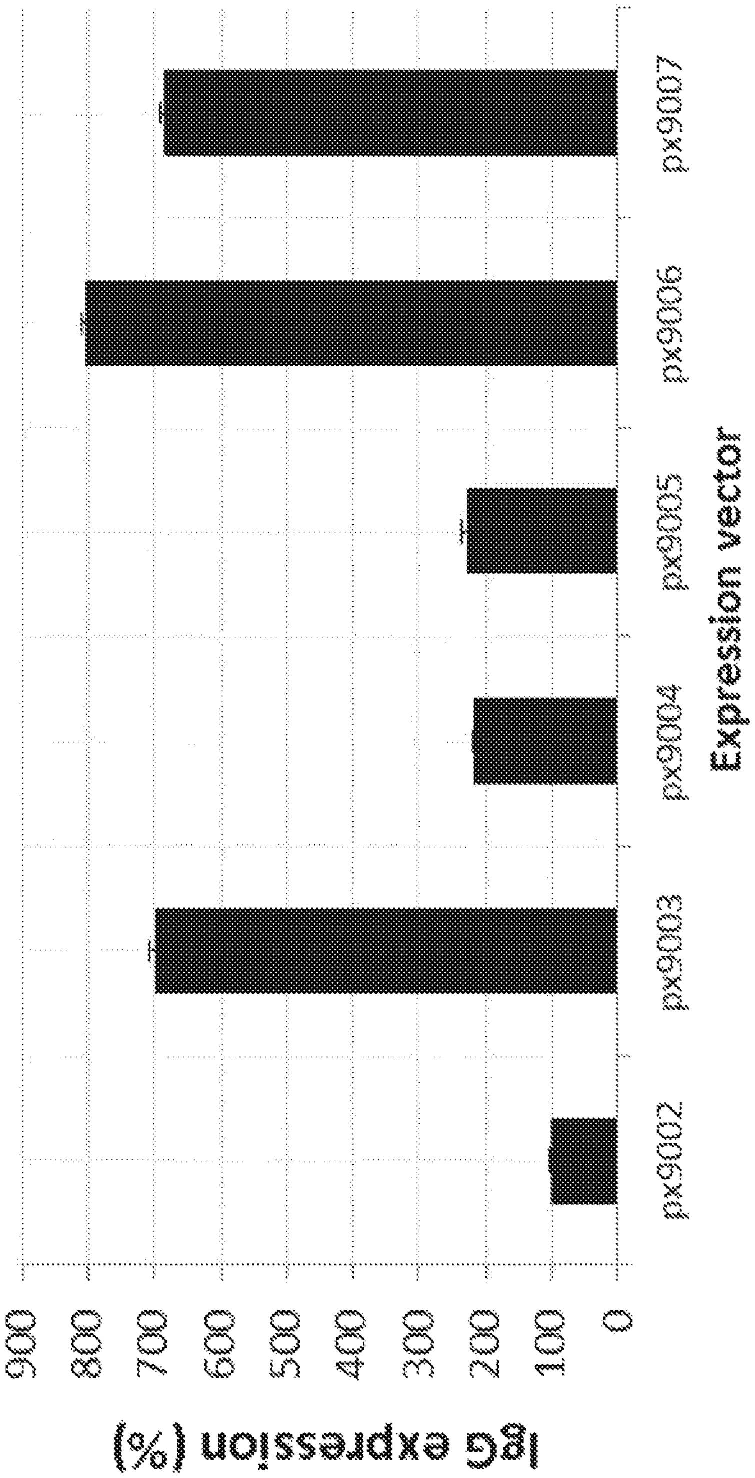

FIG. 10 Overview on product titer of stable pools generated with vectors px9001-px9007 in batch analysis on day 10. Shown is the average of two (px9001 and px9002) to three independent transfections each vector.

EXAMPLES

Expression Vector p5068 and p5069

Expression plasmids p5068 and p5069 comprise expression cassettes for the expression of an anti-P-selectin antibody (genomically organized expression cassette with retained exon-intron organization) as reported in WO 2005/100402.

The anti-P-selectin HuMab light and heavy chain encoding genes were separately assembled in mammalian cell expression vectors.

Thereby the gene segments encoding the anti-P-selectin HuMab light chain variable region (VL) and the human κ-light chain constant region (CL) were joined as were gene segments for the anti-P-selectin HuMab heavy chain variable region (VH) and the human γl-heavy chain constant region or the human γ4-heavy chain constant region (CH1-Hinge-CH2-CH3).

General information regarding the nucleotide sequences of human light and heavy chains from which the codon usage can be deduced is given in: Kabat, E. A., et al., Sequences of Proteins of Immunological Interest, 5th ed., Public Health Service, National Institutes of Health, Bethesda, Md. (1991), NIH Publication No 91-3242.

The transcription unit of the anti-P-selectin HuMab κ-light chain is composed of the following elements:

- the immediate early enhancer and promoter from the human cytomegalovirus (hCMV),
- a synthetic 5'-UT including a Kozak sequence,
- a murine immunoglobulin heavy chain signal sequence including the signal sequence intron,
- the cloned anti-P-selectin HuMab variable light chain cDNA arranged with a unique BsmI restriction site at the 5' end and a splice donor site and a unique NotI restriction site at the 3' end,
- the genomic human κ-gene constant region, including the intron 2 mouse Ig-κ enhancer (Picard, D., and Schaffner, W. Nature 307 (1984) 80-82), and
- the human immunoglobulin κ-polyadenylation (“poly A”) signal sequence.

The transcription unit of the anti-P-selectin HuMab γl-heavy chain is composed of the following elements:

- the immediate early enhancer and promoter from the human cytomegalovirus (hCMV),
- a synthetic 5'-UT including a Kozak sequence,
- a modified murine immunoglobulin heavy chain signal sequence including the signal sequence intron,
- the cloned anti-P-selectin HuMab variable heavy chain cDNA arranged with a unique BsmI restriction site at the 5' and a splice donor site and a unique NotI restriction site at the 3' end,
- the genomic human γl-heavy gene constant region, including the mouse Ig μ-enhancer (Neuberger, M. S., EMBO J. 2 (1983) 1373-1378), and
- the human γl-immunoglobulin polyadenylation (“poly A”) signal sequence.

Beside the anti-P-selectin HuMab κ-light chain or γl-heavy chain expression cassette these plasmids contain

- a hygromycin resistance gene,
- an origin of replication, oriP, of Epstein-Barr virus (EBV),
- an origin of replication from the vector pUC18 which allows replication of this plasmid in *E. coli*, and
- a β-lactamase gene which confers ampicillin resistance in *E. coli.*

Recombinant DNA Techniques

Cloning was performed using standard cloning techniques as described in Sambrook et al., 1999 (supra). All molecular biological reagents were commercially available (if not indicated otherwise) and were used according to the manufacturer’s instructions.

Nucleic Acid Synthesis

DNA of the different genetic elements was synthesized by Geneart AG, Regensburg.

Nucleic Acid Sequence Determination

DNA sequences were determined by double strand sequencing performed at SequiServe (SequiServe GmbH, Germany).

DNA and Protein Sequence Analysis and Sequence Data Management

The Vector NTI Advance suite version 9.0 was used for sequence creation, mapping, analysis, annotation, and illustration.

Cell Culture Techniques

CHO-K1 cells were grown in CD-CHO medium (Invitrogen Corp., Gibco®, Cat. No. 10743-011) supplemented with 1×HT supplement (Invitrogen Corp., Gibco®, Cat. No. 11067-030).

For the selection of stably transfected CHO-K1 pools/cells lines 400 to 800 μg/ml G418 or 200 to 400 μg/ml Hygromycin was added (Roche Diagnostics GmbH, Roche Applied Sciences, Germany, Cat. No.: 843555).

All cell lines were maintained in humidified incubators at 37° C. with 5% $CO_2$ under constant agitation at 120 to 140 rpm/min. Every 3 to 4 days the cells were split into fresh medium. Density and viability of the cultures was determined using the Casey TT or Cedex Hires cell counter (Roche innovates AG, Bielefeld). Transfection of cells was performed by the Amaxa nucleofection technology (Lonza GmbH, Germany).

Furthermore standard cell culture techniques were applied as described e.g. in Bonifacino, J. S., et al., (eds.), Current Protocols in Cell Biology, John Wiley and Sons, Inc. (2000).

Cell Counting and Determination of Cell Viability a) Electric Field Cell Counting System (CASY)

The CASY Technology Cell Counter, Model TT (Roche Innovatis AG, Bielefeld) uses electric current for cell counting. The Pulse Area Analysis was used to get information from signals created when a cell passes through the measuring pore in a low voltage field. The structural integrity of the cell membrane is a degree for cell viability. Dyes such as trypan blue are therefore not needed for determination of viability.

b) Automated Trypan Blue Exclusion Method (Cedex)

A Cedex HiRes system (Roche Innovatis AG, Bielefeld) was used to determine cell viabilities during pool selections and for automated cell counting.

Trypan blue is a dye that cannot enter cells through intact cell membranes. Only those cells are stained, and marked dead, which have a damaged cell membrane. The staining process, cell counting and graphical analysis of the results were performed automatically by the Cedex system by digital image recognition. Other measurement parameters are cell size, morphology and aggregation rate. With the multi sampler, up to 20 samples were measured consecutively.

Plasmid Preparation and Quality Check for Accurate Comparison of Plasmids in Transfections Transfection efficacy and therefore productivity is strongly influenced by several factors such as DNA amount and quality. To ensure equal starting conditions for each vector the DNA amount and quality of all vectors were intensively checked before transfection.

Simultaneously Preparation of Expression Vectors

All vectors were simultaneously prepared by the High Speed Maxi plasmid isolation Kit (Qiagen GMBH, Hilden) according to manufactures' instructions.

Phenol/Chloroform Purification and Ethanol Precipitation

All vectors were simultaneously purified by a phenol/chloroform purification. 500 μg each linearized plasmid DNA was mixed with 200 μl Tris-buffered 50% (v/v) phenol, 48% (v/v) chloroform, 2% (v/v) isoamyl alcohol solution and centrifuged for 1 min. at 13,000 rpm. The upper aqueous phase was then transferred into a new tube and mixed with 200 μl 96% (v/v) chloroform, 4% (v/v) isoamyl alcohol and centrifuged for 1 min. at 13;000 rpm. The upper phase was again transferred into a new tube and mixed with 1/10 (total volume) 3 M sodium acetate (pH 5.2) and 2.5 times (total volume) 100% ethanol. After mixing and incubating the reaction for 5 min. at room temperature, the mixture was centrifuged for 5 min. at 13,000 rpm in order to pellet the DNA. The supernatant was discarded and the pellet was washed with 900 μl 70% (v/v) ethanol and incubated for 5 min. at room temperature. After a final centrifugation step at maximum speed for 5 min., the supernatants were discarded and the pellets were dried and resuspended with sterile $H_2O$.

DNA Determination

The DNA amount of each vector was determined using the BioPhotometer (Eppendorf; Hamburg). DNA measurement was always performed in triplicates by using a 1:20 dilution in Tris pH 8.0).

Agarose Gel

DNA quality of each plasmid was checked on a 0.8% agarose gel. DNA degradation, vector conformations and DNA concentrations were determined. Vectors showing comparable quantities and qualities (no DNA degradation, similar supercoiled (ccc) forms, similar DNA amounts on gel) were used for transient and stable transfections.

Transient Transfections

All vectors were transfected in CHO-K1 cells by the Amaxa 96 well shuttle system (Lonza GmbH, Germany) according to manufactures' instructions. Each vector was transfected in 8 replicates. DNA amounts of transfected vector were normalized to equal molar amounts/copy numbers according to 1 μg of the reference expression plasmid (p5068 or p5069). To determine productivity cell free cell culture supernatant was analyzed for IgG titer on day 4 to 7 after transfection by a one-step universal ELISA (Dianova).

Amaxa 96 Well Shuttle System:

CHO-K1 cells growing in spinner flasks were pelleted by centrifugation at 850 rpm for 5 min. and resuspended in culture medium. Circular plasmids were plated out in 96-well nucleofection plates at equimolar concentrations according to 1 μg of the reference expression vector p5068 or p5069. Cells were then added into the plates at a concentration of $4\times10^5$ cells per well. The transfection was carried out by the Amaxa program DN-137. Cells were incubated for 10 min. after transfection and then transferred into 96 well flat-bottom incubation plates containing 200 μl culture medium. Cells were then statically cultivated. On day 4 to 6 after transfection IgG levels were determined using the one-step universal ELISA.

Stable Transfections and Generation of Recombinant CHO Cell Lines

Stable transfections were performed by the nucleofection technology (Amaxa Biosystems, Lonza cologne AG) according to manufactures' instructions. Before transfection plasmids were linearized by the restriction enzyme SgrA I. Each plasmid was transfected in duplicates or triplicates. $5\times10^6$ cells and 1.2 pmol linearized plasmid were used per single transfection. (Nucleofector Kit T, Amaxa program A33).

For transfection cells were resuspended in the Nucleofector solution T and aliquoted into 2 ml tubes. After the addition of the plasmid, the transfection was carried out by applying the pulse. Cells were then transferred into T25 tissue culture flasks containing pre-warmed 4 ml fresh medium and 4 ml conditioned medium. Selective pressure was applied 24 hours post-transfection by adding 250 μg/ml Hygromycin B.

Generation of Stable Pools

Vectors were transfected into CHO-K1 cells by Amaxa nucleofection technology and stable pools were selected using Hygromycin B or G418 as selection agent. Each transfection was performed in triplicates. For generation of stable pools, all plasmids were uniformly linearized by restriction digestion with SgrA I. The Nucleofector Kit T by Amaxa was used for carrying out stable transfections and each plasmid was transfected in triplicates.

Stable pools were established as follows: $5\times10^6$ cells and 1.2 pmol linearized plasmid were used for each transfection. Cells were resuspended in Solution T and aliquoted into 2 ml tubes. After the addition of the plasmid, the transfection was carried out by applying the pulse (Amaxa program A33). The transfected cell pools were statically cultivated in T25 tissue culture flasks containing pre-warmed 4 ml fresh medium and 4 ml conditioned medium.

After 24 h post-transfection selection pressure was applied: Cells were centrifuged for 5 min. at 800 rpm, resuspended in 3 ml culture medium containing 300 μg/ml Hygromycin B. Cells were transferred into flat-bottom 6-well plates 3 days post-transfection. Cells were then cultivated for two weeks till cell viabilities dropped to a minimum and rose again over 99%. Cell numbers and viabilities were constantly determined with a Cedex HiRes system (Innovatis, Bielefeld). During cultivation, cell debris was removed by centrifugation and cells were always resuspended in 3 ml fresh medium.

Generation of Stable Clones Using the Caliper Robotic System

Vectors were transfected into CHO-K1 cells as described above. 48 hours after transfection selection pressure was applied (Hygromycin B or G418) and cells were seeded onto 384 well flat-bottom plates at a concentration of 350 to 700 cells per well using an automated high-throughput clone isolation system (Sciclone ALH 3000 workstation, Caliper Life Sciences GmbH, Mainz).

After 10 to 14 days the 384 well plates were screened for IgG levels using an ELISA based ultrahigh-throughput screening (ELSIA uHTS). From a primary screening the best producing clones were chosen and transferred into flat-bottom 96 well plates. After 3 to 6 days cells were screened for IgG levels in a second round. The best producing clones again were chosen and manually transferred into flat-bottom 24 well plates. After a further ELISA based screening step the best clones were chosen and transferred into flat-bottom 6 well plates. IgG levels in the 6-well plates were determined by ProtA measurement to identify the final best clones for batch culture in shaken 6 well plates.

Batch Analysis of Pools/Single Clones

In order to detect differences in productivity and stability, cell numbers of the clones/pools were counted using a Casey cell counter and uniformly seeded into flat-bottom 6 well plates at a concentration of $3\times10^5$ cells/ml and a total volume of 3.0 ml. All batch cultures were cultivated for 12 days and cell culture supernatants were screened for human IgG levels at day 4, 7, 9, 11 or 12.

IgG Quantification

The IgG titer in transient experiments and in the screening formats (384 well to 24-well) were determined by using the one-step universal ELISA. Productivity of stable pools and stable single clones in batch experiments were determined by Protein A HPLC.

One-Step Universal ELISA

A one-step universal ELISA (Dianova) was used to determine human IgG levels from cell culture supernatants. A standard curve was prepared using serial dilutions of an anti-P-Selectin antibody (F. Hoffmann-La Roche AG, Basle, Switzerland) with a range of 0.3125-20 ng/ml using dilution buffer (PBS+5% (w/v) RPLA1). 95 µl antibody-mix containing 0.5 µg/ml biotinylated F(ab')$_2$-anti-human Fc antibody (Jackson laboratories) and 0.1 µg/ml peroxidase conjugated F(ab')$_2$-anti-human Fcγ antibody (Jackson laboratories; Suffolk) was added to streptavidin-coated 96-well MTP (StreptaWell, Roche Diagnostics GmbH). 5 µl of 1:20.000 diluted cell culture supernatant was added to the plates and incubated for 1 hour. Antibody coated plates were washed three times with 200 µl washing buffer (PBS+0.05% (v/v) Tween[20]). 100 µl ABTS (Roche Diagnostics GmbH, Mannheim, Germany) was added to the plates and the absorbance was measured at 405 nm with a reference wavelength of 492 nm.

ProtA-Measurement

The IgG titer of batch analysis were determined by Protein A using a HPLC based chromatography in combination with the one-step universal ELISA.

FACS

Fluorescence-activated cell sorting was used to determine transfection efficiencies (based on GFP expressing cells) or GFP expression levels of stably or transiently transfected cells. In general $5\times10^6$ cells of each clone or pool were measured using FACSCalibur Flow Cytometer (BD Biosciences, San Diego, Calif.). Forward and sideward scatter data were used to determine cell size, viability and cell morphology.

The invention claimed is:

1. An expression vector comprising a) an expression cassette encoding an antibody light chain, b) an expression cassette encoding an antibody heavy chain, and c) an expression cassette encoding a selection marker, wherein the expression cassettes are arranged bidirectional, wherein the expression cassette of the selection marker is arranged in the opposite direction to the antibody light chain expression cassette and antibody heavy chain expression cassette, wherein the antibody light chain expression cassette and the antibody heavy chain expression cassette are arranged unidirectional, wherein the vector is for the generation of a stable cell, and wherein the antibody light chain expression cassette and the antibody heavy chain expression cassette and optionally the selection marker expression cassette comprise a human elongation factor 1 alpha promoter.

2. The expression vector according to claim 1, characterized in that all three expression cassettes comprise the human elongation factor 1 alpha promoter.

3. The expression vector according to claim 1, characterized in that the human elongation factor 1 alpha promoter has a nucleic acid sequence of SEQ ID NO: 04, 05 or 06.

4. The expression vector according to claim 1, characterized in that the expression cassettes do not comprise a terminator sequence.

5. The expression vector according to claim 1, characterized in that one, two, or three expression cassettes comprise a bovine growth hormone polyA signal sequence.

6. The expression vector according to claim 1, characterized in that one, two, or all three expression cassettes comprise a human gastrin terminator sequence after a polyA signal sequence.

7. The expression vector according to claim 1, characterized in that the promoter of one, two, or all three expression cassettes comprise an Intron A.

8. The expression vector according to claim 1, characterized in that one, two, or all three expression cassettes comprise a SV40 polyA signal sequence.

9. The expression vector according claim 1, characterized in that the expression cassette encoding the antibody light chain and/or the expression cassette encoding the antibody heavy chain comprises at least one intron.

10. The expression vector according to claim 1, characterized in that the expression cassette encoding the antibody light chain and/or the expression cassette encoding the antibody heavy chain comprises cDNA.

11. The expression vector according to claim 1, characterized in that the expression vector is encoding a bispecific antibody.

12. A method for the production of an antibody comprising the following steps:

a) cultivating a eukaryotic cell that has been transfected with an expression vector according to claim 1, and
b) recovering the antibody from the cell or the cultivation medium.

13. The method according to claim 12, characterized in that the cell is a CHO cell.

14. The method according to claim 12, characterized in that the cell is a CHO-K1 cell.

15. A method for the generation of a stable cell comprising the following steps:

a) transfecting a eukaryotic cell with the vector according to claim 1,
b) cultivating the transfected cell in the presence of selection pressure, and
c) selecting a cell growing in the presence of selection pressure.

16. The method according to claim 15, characterized in that the cell is a CHO cell.

17. The method according to claim 15, characterized in that the cell is a CHO-K1 cell.

* * * * *